(12) United States Patent
Su et al.

(10) Patent No.: US 8,435,947 B2
(45) Date of Patent: May 7, 2013

(54) ENDOTHELIAL NITRIC OXIDE SYNTHASE ANTAGONISTS AND USES THEREOF FOR INHIBITING OXYGEN TOXICITY

(75) Inventors: Yunchao Su, Martinez, GA (US); Dmitry Kondrikov, Evans, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 13/103,667

(22) Filed: May 9, 2011

(65) Prior Publication Data

US 2012/0115785 A1    May 10, 2012

Related U.S. Application Data

(60) Provisional application No. 61/332,970, filed on May 10, 2010.

(51) Int. Cl.
*A61K 38/06* (2006.01)
(52) U.S. Cl.
USPC ....................................................... 514/15.1

(58) Field of Classification Search ........................ None
See application file for complete search history.

(56) References Cited

U.S. PATENT DOCUMENTS

2002/0058615 A1 * 5/2002 Wong et al. ........................ 514/6
2003/0040472 A1 * 2/2003 Larsen et al. ..................... 514/12

OTHER PUBLICATIONS

Kondrikov et al., Journal of Biological Chemistry, Feb. 12, 2010, vol. 285, No. 7, p. 4319-4327.*
Charles et al., Proc Natl Acad Sci U S A. Dec. 1, 1993; 90(23), p. 11419-23.*

* cited by examiner

*Primary Examiner* — Marcela M Cordero Garcia
*Assistant Examiner* — Kaipeen Yang
(74) *Attorney, Agent, or Firm* — Pabst Patent Group LLP

(57) ABSTRACT

Compositions and methods for inhibiting the interaction between eNOS and β-actin are provided for use in inhibiting or reducing lung injury from oxygen toxicity. One embodiment provides a synthetic or recombinant polypeptide having the β-actin binding domain of eNOS, wherein the polypeptide inhibits or reduces eNOS activity in lung endothelial cells.

32 Claims, 20 Drawing Sheets

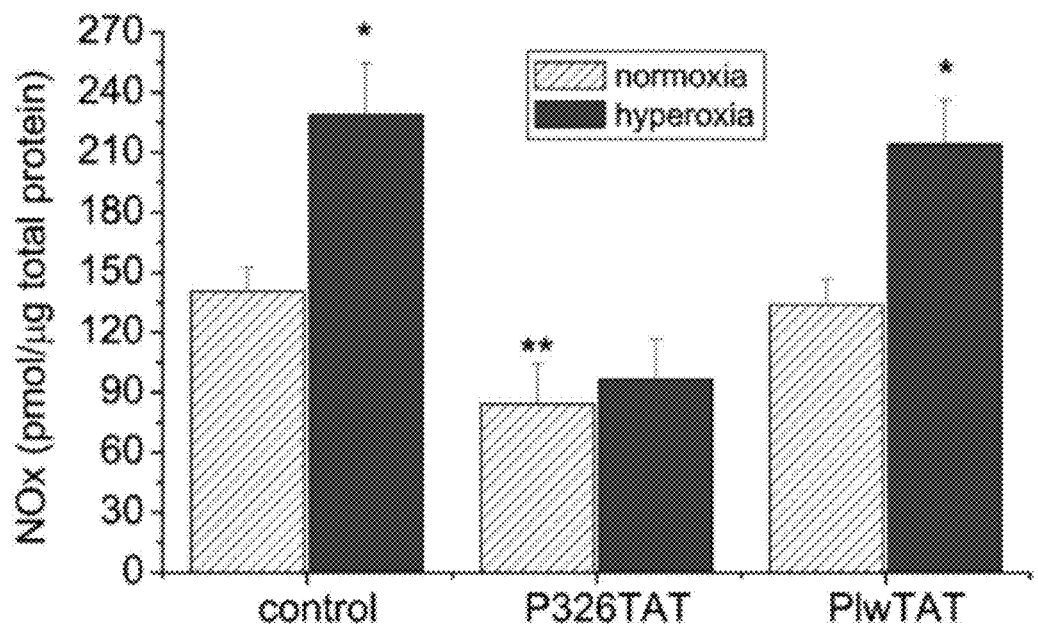
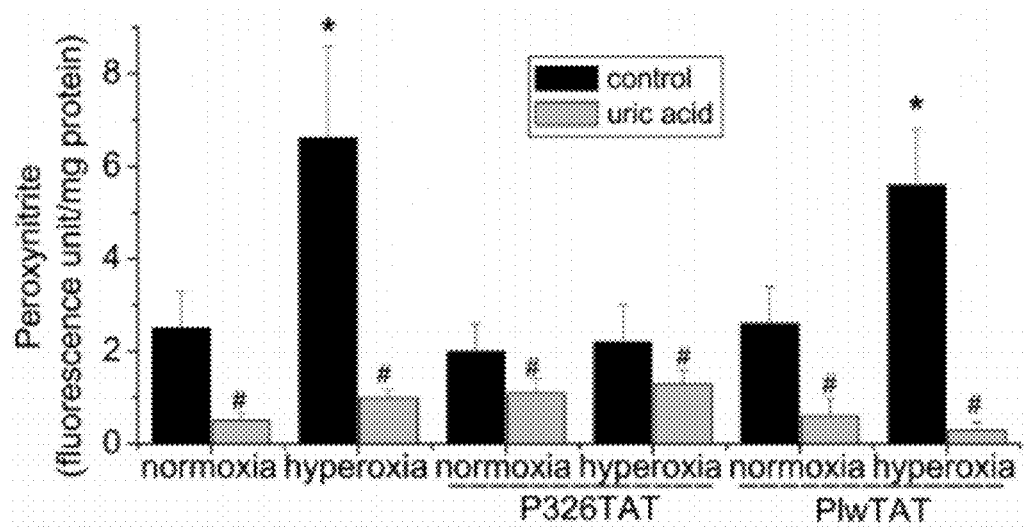

ENDOTHELIAL NITRIC OXIDE SYNTHASE ANTAGONISTS AND USES THEREOF FOR INHIBITING OXYGEN TOXICITY

CROSS REFERENCE TO RELATED APPLICATIONS

This application claims benefit of U.S. Provisional Application No. 61/332,970, filed May 10, 2010, which is hereby incorporated herein by reference in its entirety.

STATEMENT REGARDING FEDERALLY SPONSORED RESEARCH OR DEVELOPMENT

This invention was made with Government Support under Agreement R01HL088261 awarded to Yunchao Su by the National Institutes of Health. The Government has certain rights in the invention.

REFERENCE TO SEQUENCE LISTING

The Sequence Listing submitted May 9, 2011 as a text file named "MCG_2010_038_ST25.txt," created on Mar. 3, 2011, and having a size of 11,108 bytes is hereby incorporated by reference pursuant to 37 C.F.R. §1.52(e)(5).

FIELD OF THE INVENTION

The invention is generally directed to compositions and methods for inhibiting or reducing oxygen toxicity, for example using β-actin binding domain of endothelial nitric oxide synthetase (eNOS) to inhibit or reduce oxygen toxicity in the lungs.

BACKGROUND OF THE INVENTION

Although oxygen is required to sustain life, the physical characteristics of oxygen also make it potentially harmful to life. For example, oxygen toxicity can occur when 100% oxygen is inspired at normal atmospheric pressure (Jackson, R. M., Chest, 86(6):900-905 (1985)) or when breathing molecular oxygen ($O_2$) at elevated partial pressures (Allen, B. W., et al., J. Appl Physiol, 106:662-667 (2009)). Individuals at risk for developing pulmonary oxygen toxicity include scuba divers, individuals on high concentrations of supplemental oxygen (particularly premature infants), and those undergoing hyperbaric oxygen therapy.

Oxygen toxicity occurs when higher than typical physiological concentrations of oxygen lead to increased levels of reactive oxygen species (ROS). Oxygen can be reduced in the body by one or two electrons to form ROS which are natural by-products of the normal metabolism of oxygen and have important roles in cell signaling. When oxygen is breathed at high partial pressures, a hyperoxic condition will rapidly spread, with the most vascularized tissues being most vulnerable. During times of environmental stress, levels of ROS can increase dramatically, which can damage cell structures and produce oxidative stress.

One of the most reactive ROS products of oxidative stress is the hydroxyl radical (OH), which can initiate a damaging chain reaction of lipid peroxidation in the unsaturated lipids within cell membranes. High concentrations of oxygen also increase the formation of other ROS free radicals, such as nitric oxide (NO), superoxide anion ($.O^{2-}$), perhydroxy radical (HOO.), peroxynitrite, and trioxidane, which harm DNA and other biomolecules. Although the body has many antioxidant systems such as glutathione that guard against oxidative stress, these systems are eventually overwhelmed at very high concentrations of free oxygen, and the rate of cell damage exceeds the capacity of the systems that prevent or repair it. (Allen, B. W., et al., J. Appl Physiol, 106:662-667 (2009)). Cell damage and cell death can then result.

Increased generation of ROS can occur as a result of many conditions affecting newborn infants including hyperoxia, reperfusion, or inflammation. Supplemental oxygen in premature infants contributes to the development of chronic lung disease (bronchopulmonary dysplasia (BPD)), characterized by dysregulated inflammation and altered expression of proteases and growth factors (Davis, et al., Seminars in Fetal & Neonatal Medicine, 15:191-195 (2010)). More specifically, the high pressures of oxygen delivery result in necrotizing bronchiolitis and alveolar septal injury, further compromising oxygenation of blood.

Hyperoxia may also be a contributing factor for the disorder called retrolental fibroplasia or retinopathy of prematurity (ROP) in infants. In preterm infants, the retina is often not fully vascularised. Retinopathy of prematurity occurs when the development of the retinal vasculature is arrested and then proceeds abnormally. Associated with the growth of these new vessels is fibrous tissue (scar tissue) that may contract to cause retinal detachment.

Currently, the preferred way to manage oxygen toxicity is to monitor the amount of oxygen delivered to the subject. Other therapies include the administration of antioxidants, enzymes that help produce antioxidants, or compounds that stimulate the production of antioxidants to a subject. These additional therapies have had limited success.

Despite the possible toxic effects of oxygen therapy, the need for supplemental oxygen therapy remains.

It is therefore an object of the invention to provide compositions and methods for inhibiting, reducing, or preventing oxygen toxicity in a subject.

It is another object of the invention to provide compositions and methods for inhibiting or reducing pulmonary oxygen toxicity.

SUMMARY OF THE INVENTION

Compositions and methods for inhibiting the intracellular interaction between eNOS and β-actin are provided. The compositions can be used for inhibiting or reducing lung injury due to oxygen toxicity. It has been discovered that increased association of endothelial nitric oxide synthases (eNOS) with β-actin in pulmonary artery endothelial cells (PAEC) contributes to hyperoxia-induced increase in the production of nitric oxide and peroxynitrite which can cause lung damage. One embodiment provides an agent that inhibits or reduces the association between eNOS and β-actin in a subject. Suitable inhibitory agents include small molecules or polypeptides that mask eNOS binding sites on actin, compete for eNOS binding sites on actin, mask actin binding sites on eNOS, compete for actin binding sites on eNOS, or a combination thereof. Another embodiment provides a synthetic or recombinant eNOS polypeptide fragment containing the β-actin binding domain of eNOS, wherein the synthetic or recombinant eNOS fragment does not possess the ability to increase or promote the production of reactive oxygen species such as nitric oxide, peroxynitrite, or a combination of ROS. An exemplary eNOS fragment inhibits the association between endogenous eNOS and β-actin in lung endothelial cells without increasing or promoting production of ROS relative to a control. Controls include, for example biologically active eNOS polypeptides.

In certain embodiments, the β-actin binding domain of eNOS has the amino acid sequence SEQ ID NO:1 (LGLR-WYAL), or a conservative variant thereof. In preferred embodiments, the polypeptide further includes a cell penetrating peptide, such as TAT. For example a representative synthetic or recombinant polypeptide includes the amino acid sequence SEQ ID NO:2 (RKKRRQRRRALGLRWYAL) or a conservative amino acid substitution thereof. In certain embodiments, truncated forms of the actin binding site SEQ ID NO:1 can be used provided the sequence still binds actin under physiological conditions. Other cell penetrating polypeptides include a plurality of amino acids that are positively charged under physiological conditions, for example, at least 5-7, 8-15, preferably 11, consecutive, positively charged amino acids.

Another embodiment provides an isolated polypeptide of 30 residues or less having an amino acid sequence that is at least 75% identical to SEQ ID NO:1, wherein the polypeptide binds β-actin under physiological conditions. For example, in certain embodiments, the polypeptide includes at least 6 contiguous amino acids of SEQ ID NO:1 and binds to intracellular β actin under physiological conditions.

Still another embodiment provides a pharmaceutical composition containing an effective amount of the disclosed polypeptides that inhibit the interaction between eNOS and β-actin in vivo and a pharmaceutically acceptable excipient.

Yet another embodiment provides a method of inhibiting eNOS association with β-actin in a cell, including contacting the cell with a polypeptide of 30 amino acids or less having the amino acid sequence SEQ ID NO:1, or a conservative amino acid substitution or deletion thereof.

One embodiment provides a method of inhibiting or reducing ROS, for example, peroxynitrite formation in a cell by contacting the cell with a polypeptide containing the β-actin binding domain of eNOS, wherein the polypeptide inhibits eNOS activity in the cell relative to control. An exemplary control includes but is not limited to an eNOS polypeptide that does not bind to β actin.

Another embodiment provides a method of inhibiting, reducing or attenuating hyperoxia-induced lung damage in a subject, by administering to the subject a therapeutically effective amount of an agent that inhibits or reduces the intracellular association between eNOS and β actin. Exemplary inhibitory agents include polypeptides that bind to β actin and inhibit or reduce the association of eNOS with β actin bound to the polypeptide. Preferred β actin binding polypeptides contain the binding domain of eNOS or an equivalent thereof and does not increase or promote the production of ROS.

BRIEF DESCRIPTION OF THE DRAWINGS

FIGS. 12A-D are bar graphs showing the effect of the synthetic peptide P326TAT on eNOS-β-actin interaction (FIG. 12A), hyperoxia-induced increase in eNOS activity (12B), formation of NO (FIG. 12C), and formation of peroxynitrite (FIG. 12D). PAEC were incubated with or without P326TAT or PlwTAT at final concentration 20 µM and then exposed to normoxia or hyperoxia (95% oxygen) for 24 h. eNOS-β-actin association (FIG. 12A), eNOS activity (FIG. 12B), NO (FIG. 12C), and peroxynitrite (FIG. 12D) were determined. Results are expressed as mean±S.D.; n=3 experiments. *, p<0.05 versus normoxia; **, p<0.05 versus normoxia in PlwTAT group; #, p<0.05 versus control (without uric acid).

DETAILED DESCRIPTION OF THE INVENTION

I. Definitions

Figure 1A:
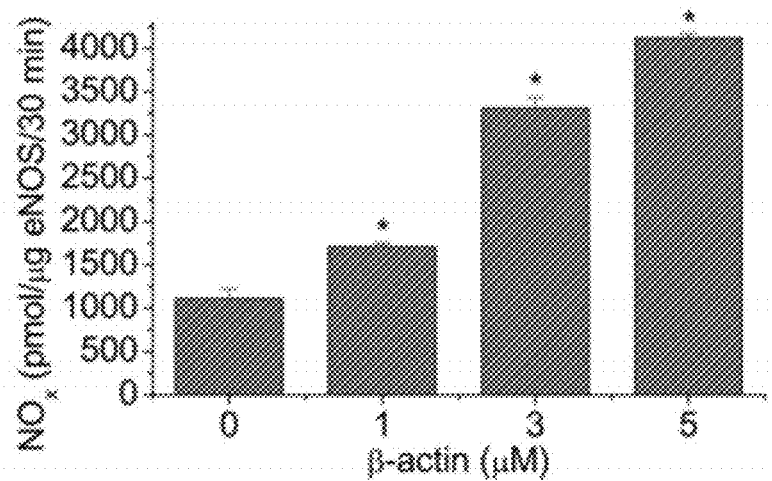
FIG. 1A is a bar graph showing $NO_x$ ($NO_2$ and $NO_3$) production (pg/μg eNOS/30 min) as a function of β-actin at 0, 1, 3, and 5 μM.

The term "β-actin-binding site" is used to refer to the amino acid residues within eNOS that are involved in the association between eNOS and β-actin, including but not limited to amino acid residues 326-333 of human eNOS protein.

The term "peptide" or "polypeptide" may be used to refer to a natural or synthetic molecule having two or more amino acids linked by the carboxyl group of one amino acid to the alpha amino group of another. The term "peptide" is not limited by length; thus "peptide" can include oligopeptide, polypeptide, gene product, expression product, or protein. The polypeptide can be a mature polypeptide meaning that the signal sequence is deleted.

The term "isolated polypeptide" refers to a polypeptide that is substantially free from the materials with which the polypeptide is normally associated in nature. The disclosed polypeptides, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides, including natural or synthetic polypeptides.

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc. Use of peptidomimetics can involve the incorporation of a non-amino acid residue with non-amide linkages at a given position. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "residue" or "position," with respect to an amino acid residue in a polypeptide, refers to a number corresponding to the numerical place that residue holds in the polypeptide. By convention, residues are counted from the amino terminus to the carboxyl terminus of the polypeptide. Thus, position 326 of human eNOS would be the 326th residue from the amino terminus of the eNOS protein sequence.

The term "protein domain" refers to a portion or portions of a protein having a specific biological activity. Proteins or polypeptides can have more than one protein domains. With regard to eNOS, an exemplary protein domain contributes to superoxide or NO production or a combination thereof. In a preferred embodiment, the protein domain participates in β-actin binding. The term can include non-contiguous amino acids within a protein that act in concert to perform the specific activity. Activities of a protein domain include, but are not limited to, homophilic and heterophilic binding to other proteins and enzymatic function.

The term "variant" refers to an amino acid or peptide sequence having conservative and non-conservative amino acid substitutions, insertions or deletions. Substitutions, deletions, insertions or any combination thereof may be combined to arrive at a final construct. The term "conservative variant" refers to one or more conservative amino acid substitutions or deletions.

"Functional variants" of the disclosed polypeptide include those that inhibit binding between β-actin and endogenous eNOS.

The term "percent (%)sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

A "chimeric molecule" is a single molecule created by joining two or more molecules that exist separately in their native state. The single, chimeric molecule has the desired functionality of all of its constituent molecules. Frequently, one of the constituent molecules of a chimeric molecule is a "targeting molecule" or "targeting moiety." The targeting molecule is a molecule such as a ligand or an antibody that specifically binds to its corresponding target, for example a receptor on a cell surface.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

By "effector molecule" is meant a substance that acts upon the target cell(s) or tissue to bring about a desired effect. The effect can, for example, be the labeling of the target cell(s) or tissue.

The term "polynucleotide" or "nucleic acid sequence" refers to a natural or synthetic molecule having two or more nucleotides linked by a phosphate group at the 3' position of one nucleotide to the 5' end of another nucleotide. The term is not limited by length and can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative or operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

The term "cell" refers to individual cells, cell lines, primary culture, or cultures derived from such cells unless specifically indicated. A "culture" refers to a composition having isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "subject" means any individual who is the target of administration. The subject can be a vertebrate, for example, a mammal. Thus, the subject can be a human. The term does not denote a particular age or sex. A patient refers to a subject afflicted with a disease or disorder. The term "patient" includes human and veterinary subjects.

"Inhibit," "inhibiting," and "inhibition" mean to decrease an activity, response, condition, disease, or other biological parameter. This can include but is not limited to the complete ablation of the activity, response, condition, or disease. This may also include, for example, a partial reduction in the activity, response, condition, or disease as compared to the native or control level. Thus, the reduction can be a 5, 10, 20, 30, 40, 50, 60, 70, 80, 90, 100%, or any amount of reduction in between as compared to native or control levels. With regard to eNOS, the reduction of activity includes partial or complete reduction in (1) binding between β-actin and eNOS; (2) NO production; or (3) both 1 and 2.

Thus, "inhibiting the binding of between eNOS and β-actin" in a cell can be a 10, 20, 30, 40, 50, 60, 70, 80, 90, 100%, or any amount of reduction in between, in the binding between eNOS and β-actin in the cell under physiological conditions as compared to native or control levels.

Likewise, "promote superoxide ($O_2^-$) generation by the cell" can be a 5, 10, 20, 30, 40, 50, 60, 70, 80, 90, 100%, or any amount of increase in between, in superoxide ($O_2$) generation as compared to native or control levels.

"Promote," "promotion," and "promoting" refer to an increase in an activity, response, condition, disease, or other biological parameter. This can include, but is not limited to, the initiation of the activity, response, condition, or disease. This may also include, for example, a 10% increase in the activity, response, condition, or disease as compared to the native or control level. Thus, the increase can be a 5, 10, 20, 30, 40, 50, 60, 70, 80, 90, 100%, or any amount of increase in between as compared to native or control levels.

The term "treat" or "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" does not require absolute forestalling of the condition or disease but can also include a reduction in the onset or severity of the disease or condition. Thus, if a therapy can treat a disease in a subject having symptoms of the disease, it can also prevent that disease in a subject who has yet to suffer some or all of the symptoms.

The term "native or control" levels refers to the levels of activity, for example, binding between eNOS and β-actin, nitric oxide (NO) generation, superoxide ($O_2^-$) generation, or peroxynitrite production, that is commonly found in similar cells under similar conditions. The native or control level can be a known or separately determined reference value. Thus, the native or control level can, but need not necessarily be determined in conjunction with the inhibited levels.

The term "therapeutically effective" means that the amount of the composition used is of sufficient quantity to ameliorate one or more causes or symptoms of a disease or disorder, such as oxygen toxicity of the lung. Such amelioration only requires a reduction or alteration, not necessarily elimination.

By "pharmaceutically acceptable" is meant a material that is not biologically or otherwise undesirable, i.e., the material may be administered to a subject, along with the disclosed polypeptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The term "reactive oxygen species" of ROS refers to

II. Compositions

Inhibition of hyperoxia-induced lung damaged can be achieved by administering one or more agents that inhibit or reduce the intracellular association between eNOS and β actin. These inhibitory agents include small molecules as well as polypeptides. In certain embodiment, the inhibitory agents can bind to or mask binding sites of eNOS on β actin or the inhibitory agents can bind to or mask β actin binding sites on eNOS. It will be appreciated that eNOS or β actin can contain more than one binding site for each other. The one or more agents inhibit the intracellular association between eNOS and β-actin, for example in pulmonary artery endothelial cells. These inhibitory polypeptides can in some embodiments compete for the binding of eNOS to β-actin or β actin to eNOS. In preferred embodiments the polypeptides include the β-actin-binding domain of eNOS or an equivalent thereof without having the ability to increase or promote ROS production. In still other embodiments the polypeptides include the eNOS-binding domain of β-actin.

The disclosed polypeptides can also contain additional moieties, such as linkers, cell penetrating peptides, cell targeting peptides, enzymatic domains, labels, radioisotopes, or a combination thereof.

A. Inhibitory Peptide

1. Nitric Oxide Production

Nitric oxide (NO) generated by endothelial NO synthase (eNOS) plays an important role in a number of physiological and pathophysiological processes including regulation of vascular tone, smooth muscle cell proliferation, and angiogenesis (Moncada, S., and Higgs, A. (1993) N. Engl. J. Med. 329, 2002-12; Michel, T., and Feron, O. (1997) J. Clin. Invest. 100, 2146-52; Papapetropoulos, A., et al. (1999) Cardiovasc. Res. 43, 509-20; Ignarro, L. J., et al. (1987) Proc. Natl. Acad. Sci. U.S.A. 84, 9265-92). The synthesis of NO requires NADPH, tetrahydrobiopterin ($BH_4$), flavin adenine dinucleotide (FAD), flavin mononucleotide (FMN), and $O_2$ as cofactors and results in NO and the co-product L-citrulline (Moncada, S., and Higgs, A. (1993) N. Engl. J. Med. 329, 2002-12). eNOS is tightly regulated by transcriptional, post-transcriptional, and post-translational mechanisms (Su, Y., et al. (2005) Cell Biochem. Biophys. 43, 439-49; Su, Y., Kondrikov, D., and Block, E. R. (2007) Sci. STKE 2007, e52-1-e52-3). Protein-protein interactions represent an important post-translational mechanism for eNOS regulation (Su, Y., et al. (2005) Cell Biochem. Biophys. 43, 439-49).

2. β-actin/eNOS Binding eNOS is associated with β-actin in endothelial cells and that association of eNOS with β-actin increases eNOS activity (Su, Y., Kondrikov, D., and Block, E. R. (2007) Sci. STKE 2007, e52-1-e52-3; Kondrikov, D., et al. (2006) Am. J. Physiol. Lung Cell Mol. Physiol. 290, L41-50; Su, Y., et al. (2003) Am. J. Physiol. Cell Physiol. 284, C1542-49). In endothelial cells, β-actin exists in two forms: filamentous polymerized actin (F-actin) and globular actin (G-actin) (dos Remedios, C. G., et al. (2003) Physiol. Rev. 83, 433-73). In lung endothelial cells, F-actin is in the form of cortical F-actin and actin stress fibers (Dudek, S. M., and Garcia, J. G. (2001) J. Appl. Physiol. 91, 1487-1500). There is a significant amount of eNOS in the insoluble portion of the Triton extraction of endothelial cells (F-actin) (Venema, V. J., et al. (1996) Biochem. Biophys. Res. Commun. 226, 703-10).

When eNOS is localized to the plasma membrane, it is colocalized with cortical F-actin. eNOS that is located in the perinuclear area is colocalized with G-actin (Su, Y., et al. (2005) Cell Biochem. Biophys. 43, 439-49; Su, Y., Kondrikov, D., and Block, E. R. (2007) Sci. STKE 2007, e52-1-e52-3; Kondrikov, D., et al. (2006) Am. J. Physiol. Lung Cell Mol. Physiol. 290, L41-50; Su, Y., et al. (2003) Am. J. Physiol. Cell Physiol. 284, C1542-49). eNOS and actin in endothelial cells can be co-immunoprecipitated, indicating that eNOS is associated with β-actin protein (Su, Y., et al. (2003) Am. J. Physiol. Cell Physiol. 284, C1542-49). Studies using a yeast two-hybrid system showed that eNOS has direct interaction with β-actin (Kondrikov, D., et al. (2006) Am. J. Physiol. Lung Cell Mol. Physiol. 290, L41-50; Kondrikov, D., et al. (2004) FASEB J. 15, 1026). Incubation of purified eNOS with F-actin and G-actin results in significant increases in eNOS activity (Su, Y., et al. (2003) Am. J. Physiol. Cell Physiol. 284, C1542-49).

The mechanism for actin association with eNOS to increase eNOS activity was not previously clear. The actin-binding site on eNOS had not previously been identified. eNOS contains two functional domains: an N-terminal oxygenase domain containing a heme active site, L-arginine-binding site, and $BH_4$-binding site; and a C-terminal reductase domain that contains the FAD-binding site, FMN-binding site, and NADPH-binding site (Chen, P. F., and Wu, K. K. (2003) J. Biol. Chem. 278, 52392-400; Abu-Soud, H. M., et al. (2000) J. Biol. Chem. 275, 17349-57). The heme site is responsible for the dimer formation of eNOS. The reductase domain of eNOS shares a close homology with the cytochrome P450 enzymes, generating electron flow from NADPH through FAD and FMN that is transferred to the oxidase domain of the other monomer where L-arginine oxidation occurs at the heme group in the active site.

The eNOS oxygenase domain rather than the reductase domain or the middle part of the eNOS molecule can have direct interaction with β-actin, indicating that the β-actin binds to the oxygenase domain of the eNOS protein (Kondrikov, D., et al. (2006) Am. J. Physiol. Lung Cell Mol. Physiol. 290, L41-50).

Three putative actin-binding sequences (ABS) exist in the eNOS oxygenase domain. Synthetic peptides and site-directed mutagenesis were used to identify approximately amino acid residues 326-333 of human eNOS protein as being responsible for binding to β-actin. Thus, the β-actin-binding site of eNOS includes amino acid residues 326-333 of human eNOS protein. Moreover, β-actin association with eNOS shifts the enzymatic activity from superoxide formation toward NO production. Thus, modulation of NO and superoxide generation from eNOS by β-actin plays an important role in endothelial function.

One embodiment provides a method for decreasing or inhibiting ROS production, in particular NO production, in endothelial cells by contacting one or more endothelial cells with an effective amount of an agent that inhibits or reduces the intracellular association between eNOS and β actin. The agent can be a small molecule or polypeptide. Preferred inhibitory polypeptides contain an actin-binding, preferably the actin-binding site of eNOS or an equivalent thereof but do not increase or promote ROS production. Thus, one embodiment provides a method for decreasing or inhibiting NO production in endothelial cells by contacting one or more endothelial cells with a effective amount of polypeptide containing the amino acid sequence according to SEQ ID NO:1 to inhibit or reduce intracellular association between eNOS and β-actin without increasing or promoting ROS production.

Another embodiment provides a method for decreasing or inhibiting hyperoxia-induced lung damage in a subject by administering to the subject an effective amount of an agent to inhibit or reduce the intracellular association between eNOS and β-actin without increasing or promoting ROS production. Preferred agents are actin-binding polypeptides that do not increase or promote the production of ROS, for example polypeptides that are non-enzymatic.

3. Sequence of β-actin Binding Domain

Isolated polypeptides having the β-actin-binding site of eNOS or an equivalent thereof are provided. The isolated polypeptide can include a fragment of eNOS protein having at least the β-actin-binding site without other biological activities of eNOS, for example without the ability to increase or promote the production of ROS. The β-actin-binding site of eNOS typically has amino acid residues 326-333 of human eNOS protein. Thus, the actin-binding site of eNOS can include SEQ ID NO:1 (LGLRWYAL). In some embodiments, the isolated polypeptide has at least 6 consecutive amino acids of SEQ ID NO:1. In some embodiments, the isolated polypeptide has at least 7 consecutive amino acids of SEQ ID NO:1.

It is also understood that the skilled artisan can identify similar actin-binding sequences of eNOS proteins from other species using routine skill with a high expectation that these sequences will retain the ability to bind human β-actin. For example, the actin-binding sequences of eNOS proteins can be identified in a vertebrate, such as horse, pig, rabbit, dog, sheep, goat, non-human primate, cow, cat, guinea pig or rodent. For example, the disclosed isolated polypeptide can include amino acid residues 328-335 of bovine or porcine eNOS protein.

Other actin-binding proteins are known. It is therefore also understood that the actin-binding sequences for these proteins would also retain the ability to bind human β-actin and can thus be used in the disclosed compositions and methods. For example, the isolated polypeptide can include amino acid residues 108-115 of human dystrophin (SEQ ID NO:7), amino acid residues 271-278 of human plectin (SEQ ID NO:8), or amino acid residues 147-154 of human β-spectrin (SEQ ID NO:9).

These actin-binding sequences are substantially similar, differing only at four of the eight amino acids. Thus, the isolated polypeptide can include the consensus amino acid sequence $LGLX_1WX_2X_3X_4$ (SEQ ID NO:15), wherein $X_1$ is R, I, or L; $X_2$ is Y, N, or T; $X_3$ is A or I; and $X_4$ is L or I.

Moreover, a non-functional control peptide (SEQ ID NO: 13) was produced where the highly hydrophobic amino acids leucine 326, leucine 328, tryptophan 330, and leucine 333 were substituted for alanine, demonstrating the importance of these amino acids. Thus, the disclosed isolated polypeptide can include the consensus amino acid sequence $LGLX_1WX_1X_1X_1$ (SEQ ID NO:16), wherein $X_1$ is any amino acid. Thus, the disclosed isolated polypeptide can include the consensus amino acid sequence $LGLX_1WX_1X_1X_2$ (SEQ ID NO:41), wherein $X_1$ is any amino acid and $X_2$ is a very hydrophobic amino acid (F, I, W, L). Thus, the disclosed isolated polypeptide can include the consensus amino acid sequence $LGLX_1WX_1X_1L$ (SEQ ID NO:42), wherein $X_1$ is any amino acid.

Polypeptides that inhibit or reduce the intracellular association between eNOS and β actin can include more than one β actin binding domain. Preferably, the inhibitory polypeptide contains one more eNOS actin binding domains. In other embodiments, the inhibitory polypeptide includes at least one eNOS actin binding domain in combination with a different actin binding domain. For example, one embodiment is a polypeptide made of repeating units of SEQ ID NO:1, 16, 41, 42 or any combination thereof

4. Size Limits of Peptide

It is believed that the isolated polypeptide having the β-actin-binding site of eNOS or the eNOS-binding site of β-actin can function by competing with endogenous eNOS for binding to β-actin, thereby inhibiting the activity of eNOS or modulating the activity of eNOS to shift production away from the production of NO. Thus, it is understood that in one embodiment, the isolated polypeptide is not full-length eNOS and preferably lacks eNOS superoxide or NO production while maintaining β-actin binding activity.

Human eNOS has 1202 amino acids. In one preferred embodiment, the isolated polypeptide does not contain the full-length amino acid sequence of eNOS and thus is less than 1202 amino acids. Thus, in some embodiments, the isolated polypeptide is less than 1200, 1150, 1100, 1050, 1000, 950, 900, 850, 800, 750, 700, 650, 600, 550, 500, 450, 400, 350, 300, 250, 200, 150, 100, 50, 40, 30, 25, or 20 amino acids in length. The isolated polypeptide can have 6, 7, 8, 9, 10, 15, 20, 21, 22, 23, 24, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 450, 500, 550, 600, 650, 700, 750, 800, 850, 900, 950, 1000, 1050, 1100, 1150, 1200 amino acid residues or less. Optionally the amino acids contain consecutive amino acid substitutions of eNOS, but in any event contain a sufficient number of amino acids of the eNOSβ-actin binding domain to bind β-actin intracellularly. It is understood that these sizes are not exclusive and also include numbers of amino acids within the recited sizes. Therefore, in preferred embodiments, the isolated polypeptide can have 8, 9, 10, 11, 12, 13, 14, 15, 16, 17, 18, 19, 20, 25, 30, 31, 32, 33, 34, 35, 36, 37, 38, 39, 40 amino acid residues.

5. Exclusion of eNOS Domains

In some embodiments, the peptide lacks one or more functional protein domains of eNOS. For example, the oxygenase domain of eNOS is located within amino acid residues 68-480. eNOS produces nitric oxide (NO) by catalyzing a five-electron heme-based oxidation of a guanidine nitrogen of L-arginine to L-citrulline via two successive mono-oxygenation reactions. Thus, in some embodiments, the disclosed isolated polypeptide does not contain amino acid residues 68-325 or 334-480 of human eNOS. Thus, in some embodiments, the disclosed isolated polypeptide includes no more than 5, 6, 7, 8, 9, 10 consecutive amino acids found in amino acid residues 68-325 or 334-480 of human eNOS.

Human eNOS has a Ferredoxin reductase (FNR) domain, which includes FAD and NAD(P) binding regions, within amino acid residues 762-1164. The disclosed isolated polypeptide can include a fragment of eNOS lacking the C-terminal reductase domain. The isolated polypeptide optionally lacks amino acid residues 762-1164 of human eNOS. Thus, in some embodiments, the isolated polypeptide has no more than 5, 6, 7, 8, 9, 10 consecutive amino acids found in amino acid residues 762-1164 of human eNOS.

Human eNOS contains a calcium-activated calmodulin (CaM) binding region at amino acid residues 493-510, which induces a conformational change to facilitate electron transfer. Thus, in some embodiments, the disclosed isolated polypeptide lacks amino acid residues 493-510 of human eNOS. Thus, in some embodiments, the disclosed isolated polypeptide contains no more than 5, 6, 7, 8, 9, 10 consecutive amino acids found in amino acid residues 493-510 of human eNOS.

6. Functional limits of Peptide

As noted above, the peptide preferably lacks one or more functional protein domains of eNOS. Thus, in certain embodiments, the disclosed polypeptide lacks one or more activities of native eNOS. "Activities" of a protein include, for example, enzymatic activity and homophilic and heterophilic binding to other proteins.

eNOS is capable of generating both NO and superoxide. The oxygenase domain of eNOS is involved with superoxide generation when eNOS is uncoupled due to limited $BH_4$ availability. An increase in NO production induced by β-actin binding to eNOS is accompanied by a decrease in superoxide production, indicating that β-actin binding to eNOS shifts the enzymatic activity from superoxide formation toward NO production. Specific blockage of eNOS-β-actin association using ABS peptide 326 decreased β-actin-induced increase in NO production and decrease in superoxide formation and NADPH consumption in vitro. Moreover, inhibition of eNOS-β-actin association by ABS peptide 326 decreased NO production and endothelial monolayer wound repair and increased superoxide formation from eNOS in intact endothelial cells.

Thus, it is believed that eNOS-β-actin association can mediate the balance of nitric oxide (NO) and superoxide ($O_2^-$) generation from eNOS. Specifically, an increased association of eNOS with β-actin contributes to hyperoxia-induced increase in the production of peroxynitrite ($ONOO^-$) which can cause nitrosative stress in the lungs.

Thus, in some embodiments, the isolated polypeptide can inhibit the binding of eNOS to β-actin within a cell as compared to native or control level of binding. In some embodiments, the disclosed isolated polypeptide can inhibit nitric oxide (NO) generation by the cell as compared to native or control level of NO generation. Thus, in some embodiments, the isolated polypeptide can promote superoxide ($O_2^-$) generation by the cell as compared to native or control level of superoxide generation. Thus, in some embodiments, the isolated polypeptide can inhibit the production of peroxynitrite ($ONOO^-$) by the cell as compared to native or control level of peroxynitrite production.

7. Source a. Purified Fragments of eNOS or β-actin

In some embodiments, the disclosed isolated polypeptide is a fragment of human eNOS or human β-actin. In some embodiments, the polypeptide is produced by cleaving human eNOS or human β-actin into peptide fragments. As an example, human eNOS can be digested using proteases, and peptide fragments having the β-actin binding domain can be purified from the peptide extract using conventional techniques, such as, for example, antibodies that specifically bind the β-actin binding domain, chromatography, gel electrophoresis, and the like.

Thus, also disclosed are antibodies that specifically bind SEQ ID NO:1 and their use in detecting and purifying the polypeptides disclosed herein. In some embodiments, these antibodies are monoclonal antibodies. In some embodiments, these antibodies bind the β-actin binding domain of eNOS but not eNOS fragments lacking the β-actin binding domain. Thus, in some embodiments, these antibodies specifically bind the amino acid sequence SEQ ID NO:1 but not to any fragments of eNOS not having the amino acid sequence SEQ ID NO:1.

b. Synthetic Polypeptide

In some embodiments, the disclosed polypeptide that inhibits eNOS binding to β-actin is synthetic. In these embodiments, one or more of the amino acids of the polypeptide are linked together using conventional protein chemistry techniques.

The synthetic polypeptide can include the β-actin binding domain of eNOS or the eNOS-binding domain of β-actin. For example, the β-actin binding domain of eNOS can include the amino acid sequence SEQ ID NO:1, or a conservative amino acid substitution or deletion thereof.

c. Recombinant Polypeptide

In some embodiments, the disclosed polypeptide that inhibits eNOS binding to β-actin is recombinant. In these embodiments, the polypeptide is produced by culturing a cell that expresses a nucleic acid encoding the polypeptide. The nucleic acid can be operably linked to an expression control sequence under conditions suitable for the transcription and translation of the nucleic acid.

The recombinant polypeptide can also contain the β-actin binding domain of eNOS or the eNOS-binding domain of β-actin. For example, the β-actin binding domain of eNOS can include the amino acid sequence SEQ ID NO:1, or a conservative amino acid substitution or deletion thereof

8. Variants

Also disclosed are functional variants of the disclosed polypeptide that can compete with eNOS for binding to β-actin in cells. For example, the oxygenase domain of eNOS is involved with superoxide generation when eNOS is uncoupled due to limited $BH_4$ availability. An increase in NO production induced by β-actin binding to eNOS is accompanied by a decrease in superoxide production. Thus, activities of eNOS, specifically eNOS associated with β-actin, include promotion of NO and peroxynitrite production and decreasing superoxide production.

Insertions include amino and/or carboxyl terminal fusions as well as intra-sequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein sequence. Thus, the polypeptide can have 1, 2, 3, or 4 deletions from SEQ ID NO:1. These variants ordinarily are prepared by site specific mutagenesis of nucleotides in the DNA encoding the protein, thereby producing DNA encoding the variant, and thereafter expressing the DNA in recombinant cell culture.

Substitutional variants are those in which at least one residue has been removed and a different residue inserted in its place. Thus, the polypeptide can also have 1, 2, 3, or 4 substitutions within SEQ ID NO:1. Techniques for making substitution mutations at predetermined sites in DNA having a known sequence are well known, for example M13 primer mutagenesis and PCR mutagenesis.

a. Conservative Substitutions

In certain embodiments, the protein variant has a conservative amino acid substitution in SEQ ID NO:1. The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr.

In contrast, the substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

b. Percent Identity

It is understood that one way to define the variants and derivatives of the disclosed polypeptides disclosed herein is through defining the variants and derivatives in terms of homology/identity to specific known sequences. Thus, disclosed are variants of these and other disclosed proteins. For example, disclosed are polypeptides having at least, 5, 6, or 7 of the 8 amino acids in SEQ ID NO:1. Thus, disclosed are polypeptides having at least 62% (5 of 8 amino acids), 75% (6 of 8 amino acids) or 87.5% (7 of 8 amino acids) identity to SEQ ID NO:1.

Those of skill in the art readily understand how to determine the sequence identity of two proteins. For example, the sequence identity can be calculated after aligning the two sequences so that the sequence identity is at its highest level.

It is understood that the description of conservative mutations and sequence identity can be combined together in any combination, such as embodiments that have at least 75% sequence identity to a particular sequence wherein the variants are conservative mutations.

Thus, disclosed is an isolated polypeptide having an amino acid sequence that is at least 62% (5 of 8 amino acids), 75% (6 of 8 amino acids) or 87.5% (7 of 8 amino acids) identical to SEQ ID NO:1, wherein the polypeptide binds β-actin. In preferred embodiments, the isolated polypeptide having least 62% (5 of 8 amino acids), 75% (6 of 8 amino acids) or 87.5% (7 of 8 amino acids) sequence identity to SEQ ID NO:1 binds to β-actin in vivo.

9. Analogs and Mimetics

It is understood that there are numerous amino acid and peptide analogs which can be incorporated into the disclosed compositions. Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

Thus, also disclosed is a peptidomimetic of the disclosed polypeptides that can compete for eNOS binding to β-actin. Peptidomimetics typically enhance some property of the original peptide, such as increase stability, increased efficacy, enhanced delivery, increased half life, etc. Use of peptidomimetics can involve the incorporation of a non-amino acid residue with non-amide linkages at a given position. One embodiment can be a peptidomimetic wherein the compound has a bond, a peptide backbone or an amino acid component replaced with a suitable mimic.

a. Non-Natural Amino Acids

Some non-limiting examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

There are also numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way. D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides.

b. Modified Amino Acid Linkages

Molecules can be produced that resemble peptides, but which are not connected via a natural peptide linkage. For example, linkages for amino acids or amino acid analogs can include —CH₂NH—, —CH₂S—, —CH₂—CH₂—, —CH═CH— (cis and trans), —COCH₂—, —CH(OH)CH₂—, and —CHH₂SO—. A particularly preferred non-peptide linkage is —CH₂NH—. It is understood that peptide analogs can have more than one atom between the bond atoms, such as b-alanine, g-aminobutyric acid, and the like.

Cysteine residues can also be used to cyclize or attach two or more peptides together. This can be beneficial to constrain peptides into particular conformations. (Rizo and Gierasch Ann. Rev. Biochem. 61:387 (1992), incorporated herein by reference).

B. Additional Moieties

Also disclosed is the linkage of additional moieties to the disclosed polypeptide that competes for the binding of eNOS to β-actin. In some embodiments, the disclosed isolated polypeptide is a chimeric molecule. In some embodiments, the disclosed isolated polypeptide is a fusion protein having a β-acting binding domain. In some embodiments, the disclosed isolated polypeptide that competes for the binding of eNOS to β-actin is linked to one or more additional moieties by a chemical linkage.

1. Multivalent Peptides

The disclosed polypeptide can be linked together to form divalent or multivalent peptides. In some embodiments, the polypeptides are directly linked together to form a polymer. Thus, disclosed is a polypeptide having two or more polypeptide sequences that compete for the binding of eNOS to β-actin. Thus, disclosed is a polypeptide having two or more amino acid sequences set forth in SEQ ID NO:1.

Two or more of the disclosed polypeptide can be linked together to form a conjugate. For example, disclosed is a composition including a first polypeptide having the amino acid sequence SEQ ID NO:1, or a conservative substitution or deletion thereof, and a second polypeptide having the amino acid sequence SEQ ID NO:1, or a conservative substitution or deletion thereof, wherein the first and second polypeptides are conjugated together with a linker. The linker can be any molecule, compound, or composition capable of joining two or more polypeptides together. For example, the linker can be one or more amino acids. The linker can be a polymer, such as polyethylene glycol (PEG).

Thus, disclosed is a composition having the formula:

BP-X-BP, wherein BP is a β-actin binding protein and X is a linker. Thus also disclosed is a composition having the formula:

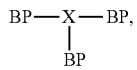

wherein BP is a β-actin binding protein and X is a linker. Other such conjugations of β-actin binding proteins can be envisioned and are disclosed.

Thus, in some embodiments, the polypeptides are linked to form a dendrimer. Peptide dendrimers are branched, often highly branched, artificial proteins in which several peptide chains branch out from a dendritic core matrix that is built up through the propagation of, for example, a trifunctional amino acid, such as Lys. Originally conceived as Multiple Antigen Presentation System (MAPs) for vaccine development, these molecules are also useful for protein design.

2. Cell-penetrating Peptides

The disclosed polypeptide can be linked to a cell penetrating peptides (also referred to as an internalization sequence or a protein transduction domain) to effectively enter the cell. In some embodiments, the disclosed isolated peptide is a fusion protein having the β-acting binding domain of eNOS operably linked to a cell penetrating peptide. In alternative embodiments, the β-acting binding domain of eNOS is linked to the cell penetrating peptide with other means, such as with a protein crosslinker Recent studies have identified several cell penetrating peptides, including the TAT transactivation domain of the HIV virus, antennapedia, and transportan that can readily transport molecules and small peptides across the plasma membrane. More recently, polyarginine has shown an even greater efficiency of transporting peptides and proteins across the plasma, membrane making it an attractive tool for peptide mediated transport.

Nonaarginine has been described as one of the most efficient polyarginine based protein transduction domains. Nonaarginine-mediated membrane transport is facilitated through heparan sulfate proteoglycan binding and endocytic packaging. Once internalized, heparan is degraded by heparanases, releasing nonaarginine which leaks into the cytoplasm.

Thus, the provided polypeptide can include a cell penetrating peptide sequence. The cell penetrating peptide sequence can be any sequence known or newly discovered in the art capable of transducing a cell. Non-limiting examples of cell penetrating peptide include Polyarginine (e.g., nonaarginine), Antennapedia sequences, TAT, HIV-Tat, R9-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 1).

TABLE 1

Cell Internalization Transporters

| Name | Sequence | SEQ ID NO |
| --- | --- | --- |
| Tat | RKKRRQRRR | SEQ ID NO: 17 |
| HIV-Tat | GRKKRRQRPPQ | SEQ ID NO: 18 |
| R9-Tat | GRRRRRRRRRPPQ | SEQ ID NO: 19 |
| HIV-1 Rev-(34-50) | TRQARRNRRRRWRERQR | SEQ ID NO: 20 |
| R7W | RRRRRRRW | SEQ ID NO: 21 |
| TatP59W | GRKKRRQRRRPWQ | SEQ ID NO: 22 |
| FHV Coat-(35-49) | RRRRNRTRRNRRRVR | SEQ ID NO: 23 |
| BMV Gag-(7-25) | KMTRAQRRAAARRNRWTAR | SEQ ID NO: 24 |

TABLE 1-continued

Cell Internalization Transporters

| Name | Sequence | SEQ ID NO |
|---|---|---|
| HTLV-II Rex-(4-16) | TRRQRTRRARRNR | SEQ ID NO: 25 |
| CCMV Gag-(7-25) | KLTRAQRRAAARKNKRNTR | SEQ ID NO: 26 |
| P22 N-(14-30) | NAKTRRHERRRKLAIER | SEQ ID NO: 27 |
| Polyarginine | RRRRRRRRR | SEQ ID NO: 28 |
| Antennapedia | RQPKIWFPNRRKPWKK | SEQ ID NO: 29 |
| Penetratin | RQIKIWFQNRRMKWKK | SEQ ID NO: 30 |
| Antp-3A | RQIAIWFQNRRMKWAA | SEQ ID NO: 31 |
| Buforin II | TRSSRAGLQFPVGRVHRLLRK | SEQ ID NO: 32 |
| Transportan | GWTLNSAGYLLGKINKALAA LAKKIL | SEQ ID NO: 33 |
| model amphipathic peptide (MAP) | KLALKLALKALKAALKLA | SEQ ID NO: 34 |
| K-FGF | AAVALLPAVLLALLAP | SEQ ID NO: 35 |
| pVEC | LLIILRRRIRKQAHAHSK | SEQ ID NO: 36 |
| Pep-1 | KETWWETWWTEWSQPKK KRKV | SEQ ID NO: 37 |
| SynB1 | RGGRLSYSRRRFSTSTGR | SEQ ID NO: 38 |
| Pep-7 | SDLWEMMMVSLACQY | SEQ ID NO: 39 |
| HN-1 | TSPLNIHNGQKL | SEQ ID NO: 40 |

Thus, in some embodiments, the cell penetrating peptide of the disclosed isolated polypeptide is TAT (SEQ ID NO:17). Thus, in some embodiments, the disclosed isolated polypeptide includes the amino acid sequence SEQ ID NO:2 (RKKRRQRRRALGLRWYAL), or a conservative variant thereof.

3. Cell Targeting/Homing a. Peptides

In some embodiments, the polypeptide is operably linked to a cell-targeting peptide to facilitate homing of the polypeptide to lung endothelial cells. For example, in some embodiments, the disclosed polypeptide can include the tripeptide motif gly-phe-glu (GFE).

b. Antibodies

In some embodiments, the polypeptide is operably linked to an antibody, antibody fragment, aptamer, or other molecule that specifically binds an endothelial antigen to facilitate homing of the polypeptide to lung endothelial cells. In some embodiments, the endothelial antigen is platelet endothelial cell adhesion molecule (PECAM; CD31), intercellular adhesion molecule-1 (ICAM-1; CD54), Thy-1.1 (CD90.1), Endothelial factor VIII, or angiotensin-converting enzyme (ACE; CD143).

Under designated conditions (e.g. immunoassay conditions in the case of an antibody), a specified ligand or antibody "specifically binds" to its particular "target" (e.g., an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $mol^{-1}$ (e.g., $10^6$ $mol^{-1}$, $10^7$ $mol^{-1}$, $10^8$ $mol^{-1}$, $10^9$ $mol^{-1}$, $10^{10}$ $mol^{-1}$, $10^{11}$ $mol^{-1}$, and $10^{12}$ $mol^{-1}$ or more) with that second molecule.

Other embodiments are directed to antibodies that specifically bind to the disclosed polypeptides or to eNOS polypeptides at the disclosed polypeptide sequence in eNOS under physiological conditions. The antibodies can be human, or humanized, monoclonal, polyclonal, bispecific, or single chain antibodies. The antibodies can be antigen binding fragments of antibodies.

4. Effector Molecules

The disclosed polypeptides and pharmaceutical compositions can further include an effector molecule. The effector molecule can, for example, be a small molecule, pharmaceutical drug, toxin, fatty acid, detectable marker, conjugating tag, nanoparticle, or enzyme. Examples of small molecules and pharmaceutical drugs that can be conjugated to a targeting peptide are known in the art.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the provided compositions.

The effector molecule can be covalently linked to the disclosed peptide. The effector molecule can be linked to the amino terminal end of the disclosed peptide. The effector molecule can be linked to the carboxy terminal end of the disclosed peptide. The effector molecule can be linked to an amino acid within the disclosed peptide. The disclosed compositions can further include a linker connecting the effector molecule and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the disclosed peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido) hexanoate), SULFO NHS LC SPDP (Sulfosuccinimidyl-643-(2-pyridyldithio) propionamido) hexanoate), SPDP(N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH(N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

5. Linkers and Tags

The provided polypeptide can have additional N-terminal, C-terminal, or intermediate amino acid sequences, e.g., amino acid linkers or tags. The term "amino acid linker" refers to an amino acid sequences or insertion that can be used to connect or separate two distinct polypeptides or polypeptide fragments, wherein the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

Thus, in some embodiments, the isolated polypeptide can include one or more amino acids linking the β-actin-binding site of eNOS to, for example, a cell penetrating peptide or cell targeting peptide. For example, in SEQ ID NO:2, the cell penetrating peptide is linked to the β-actin-binding site of eNOS by an alanine residue. Other suitable linking amino acids are known in the art and can be selected using routine skill.

C. Pharmaceutical Compositions

1. Excipients

The compositions disclosed can be used therapeutically in combination with a pharmaceutically acceptable excipient/carrier. The pharmaceutical compositions can have an effective amount of one or more polypeptides, including antibodies, disclosed herein that inhibit or reduce the intracellular association between eNOS and β-actin in vivo and a pharmaceutically acceptable excipient.

Pharmaceutical excipients are known to those skilled in the art. These most typically would be standard carriers for administration of drugs to humans, including solutions such as sterile water, saline, and buffered solutions at physiological pH. Pharmaceutical compositions may include carriers, thickeners, diluents, buffers, preservatives, surface active agents and the like in addition to the active agent. Pharmaceutical compositions may also include one or more active ingredients such as antimicrobial agents, anti-inflammatory agents, anesthetics, and the like.

Suitable pharmaceutical preparations include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Suitable formulations include sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Liposomes

Also disclosed is a pharmaceutical composition having an effective amount of one or more polypeptides disclosed herein, including antibodies, that interfere or reduce the association between eNOS and β-actin in vivo in a liposome. The term "liposome" refers to a structure having an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion.

Liposomes can also take the form of unilamnellar vesicles, which are prepared by more extensive sonication of MLVs, and are made of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. For example, sonication of an aqueous dispersion of phospholipids produces small ULVs having a lipid bilayer surrounding an aqueous solution. Liposome precursors can be made by ultrasonication, followed by the addition of an aqueous medium containing amphiphilic compounds and centrifugation to form a biomolecular lipid layer system. Small ULVs can also be prepared by an ethanol or ether injection technique, which involves the rapid injection of an organic solution of lipids into a buffer solution, which results in the rapid formation of unilamellar liposomes. A detergent removal method for making ULVs involves solubilizing the lipids and additives with detergents by agitation or sonication to produce the desired vesicles. Large ULVs can be prepared by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Agents can also be encapsulated in unilamellar vesicles by freezing/thawing an aqueous phospholipid dispersion of the agent and lipids.

In addition to the MLVs and ULVs, liposomes can also be multivesicular. These multivesicular liposomes can be spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles can have a diameter of 2-15 μm.

Fatty acids (i.e., lipids) that can be conjugated to the provided compositions include those that allow the efficient incorporation of the disclosed compositions into liposomes. Generally, the fatty acid is a polar lipid. Thus, the fatty acid can be a phospholipid. The provided compositions can include either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)—PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can include palmitoyl 16:0.

3. Articles and Devices

Also disclosed is an article or device having one or more of the disclosed polypeptides or pharmaceutical compositions. For example, disclosed is an inhaler having an effective amount of one or more disclosed polypeptides that inhibit or reduce the association between eNOS and β-actin in vivo and a pharmaceutically acceptable excipient.

An "inhaler" is a medical device used for delivering medication into the body via the lungs. There are several different types of inhalers. The most common is the pressurized metered-dose inhaler (MDI). In MDIs, medication is most commonly stored in solution in a pressurized canister that contains a propellant, although it may also be a suspension. The MDI canister is attached to a hand-operated actuator. On activation, the metered-dose inhaler releases a fixed dose of medication in aerosol form. The correct procedure for using an MDI is to first fully exhale, place the mouth-piece of the device into the mouth, and having just started to inhale at a moderate rate, depress the canister to release the medicine. The aerosolized medication is drawn into the lungs by continuing to inhale deeply before holding the breath for 10 seconds to allow the aerosol to settle onto the walls of the bronchial and other airways of the lung.

Besides the MDI, other types of inhalers include dry powder inhalers (DPIs), which release a dose of medicine as a powder aerosol that is inhaled by the patient, and nebulizers, which instead supply the aerosol as a mist created from an aqueous formulation.

Thus, the disclosed pharmaceutical compositions having one or more polypeptides that compete with eNOS binding to β-actin in vivo and a pharmaceutically acceptable excipient can be in solution or in dry powder form. Other formulations can be selected based on known methods of delivery to the lung.

4. Co-Administration

The disclosed pharmaceutical compositions can be administered to the lung (directly or indirectly) alone or in combination with other therapeutic agents or compositions. Thus, in addition to the combination therapeutic compositions, also disclosed are methods involving co-administration of the disclosed compositions and other therapeutic agents or compositions suitable for delivery to the lung.

In a preferred embodiment, the disclosed polypeptide or pharmaceutical compositions are co-administered with oxygen to inhibit or reduce the effects of hyperoxia. For example, the disclosed polypeptide or pharmaceutical compositions could be administered by a nebulizer, vaporizer, dry powder inhaler, or pressurized metered dose inhaler concurrently with oxygen when it is being used at prolonged or very high concentrations.

D. Nucleic Acids

1. Nucleic Acids Encoding the Peptides

Also disclosed are nucleic acids encoding the disclosed polypeptides. Thus, disclosed are all nucleic acids, including degenerate nucleic acids, encoding the disclosed variants and derivatives of the protein sequences. While each particular nucleic acid sequence may not be written out, it is understood that each and every sequence is in fact disclosed and described through the disclosed protein sequence.

2. Expression Control Sequences

The nucleic acids that are delivered to cells typically contain expression control systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Thus, also disclosed are nucleic acids encoding the disclosed polypeptides operably linked to an expression control sequence.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species can also be used.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and contains of about 400 bases. It is also preferred that the transcribed units contain other standard sequences alone or in combination with the above sequences improve expression from, or stability of, the construct.

3. Vectors containing the Nucleic Acids

Also disclosed is a vector containing a nucleic acid encoding the disclosed polypeptides. In some embodiments the vector is derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens.

4. Cells containing Vectors

Also disclosed are cells containing one or more of the disclosed nucleic acids or vectors. The cells can be cell lines, primary cultured cells, or cells isolated from a subject. The cells can be prokaryotic or eukaryotic. For example, bacterial cells are particularly useful for recombination and replication of vectors. In contrast, eukaryotic cells are preferable for in vitro expression peptides encoded by the vectors. Eukaryotic cells include insect and mammalian cells. In some preferred embodiments, the cells are human cells, such as lung endothelial cells.

E. Combination Therapies

Disclosed is a composition that contains the disclosed polypeptides that compete for eNOS binding to β-actin and any known or newly discovered substance that can be administered to the lung.

For example, the provided composition(s) can further include one or more of classes of antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, Vancomycin).

The provided composition(s) can further include one or more of classes of steroids (e.g., Andranes (e.g., Testosterone).

The provided composition(s) can further include one or more of classes of narcotic and non-narcotic analgesics (e.g., Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine).

The provided composition(s) can further include one or more of classes of anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Morniflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

The provided composition(s) can further include one or more of classes of anti-histaminic agents (e.g., Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

II. Methods

Disclosed are uses and methods relating to the disclosed polypeptides and pharmaceutical compositions. For example, methods are provided for using the disclosed polypeptides to inhibit the association of β-actin and eNOS. Also provided are methods of preventing, inhibiting, reducing or attenuating lung damage by hyperoxia in a subject involving administering to the subject the disclosed polypeptides and pharmaceutical compositions.

A. Uses of Inhibitory Peptide

1. Inhibiting eNOS Interaction with β-actin

Also disclosed is a method of inhibiting eNOS association with β-actin in a cell. The method can involve contacting the cell with a disclosed polypeptide or pharmaceutical composition. In a preferred embodiment, the polypeptide or pharmaceutical composition can compete for the binding of eNOS to β-actin in the cell. In a preferred embodiment, an effective amount of the polypeptide or pharmaceutical composition can inhibiting or reducing damage in the cell from hyperoxia. In a preferred embodiment, an effective amount of the polypeptide or pharmaceutical composition can inhibit peroxynitrite formation in the cell.

a. β-actin Binding Domain of eNOS

The disclosed method can involve contacting the cell with a polypeptide having a β-actin-binding, preferably the β actin binding site of eNOS. Thus, the method can involve contacting the cell with a polypeptide having amino acid residues 326-333 of human eNOS protein. Thus, the actin-binding site of eNOS can include SEQ ID NO:1 (LGLRWYAL). In some embodiments, the isolated polypeptide has at least 6 consecutive amino acids of SEQ ID NO:1. In some embodiments, the isolated polypeptide has at least 7 consecutive amino acids of SEQ ID NO:1. In some embodiments, the polypeptide is 30 amino acids or less and contains the amino acid sequence SEQ ID NO:1, or a conservative variant thereof.

In some embodiments, the polypeptide contains a cell penetrating peptide. For example, the cell penetrating peptide can be TAT. Thus, some embodiments, the polypeptide has amino acid sequence SEQ ID NO:2, or a conservative variant thereof.

In some embodiments, the polypeptide includes a lung-homing peptide. For example, the lung-homing peptide can be the tripeptide motif gly-phe-glu (GFE).

b. eNOS Binding Domain of β-actin

The disclosed method can involve contacting the cell with a polypeptide having the eNOS-binding site of β-actin. In some embodiments, the polypeptide contains a cell penetrating peptide. For example, the cell penetrating peptide can be TAT. In some embodiments, the polypeptide includes a lung-homing peptide. For example, the lung-homing peptide can be the tripeptide motif gly-phe-glu (GFE).

2. Inhibiting Lung Damage by Hyperoxia

Also disclosed is a method of inhibiting, reducing, or attenuating lung damage by hyperoxia in a subject. The method can involve administering to the subject a therapeutically effective amount of a polypeptide having a β-actin binding domain, preferably the β actin binding domain of eNOS, wherein the polypeptide does not promote or increase ROS production. Thus, fragments of eNOS can be administered.

In some embodiments of the method, the β-actin binding domain has the amino acid sequence SEQ ID NO:1 (LGLRWYAL), or a conservative variant thereof.

In some embodiments of the method, the polypeptide further includes a cell penetrating peptide. For example, in some embodiments, the cell penetrating peptide is TAT. Thus, in some embodiments, the polypeptide has the amino acid sequence SEQ ID NO:2, or a conservative variant thereof.

In some embodiments of the method, the polypeptide further includes a lung-homing peptide. For example, in some embodiments, the lung-homing peptide is the tripeptide motif gly-phe-glu (GFE).

3. Administration

The disclosed polypeptides and pharmaceutical compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically, or the like. Topical intranasal administration includes delivery of the compositions into the nose and nasal passages through one or both of the nares and can involve delivery by a spraying mechanism or droplet mechanism, or through aerosolization of the disclosed composition. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions.

The disclosed compositions that inhibit eNOS and β-actin interaction in vivo may also be administered prophylactically to patients or subjects who are at risk for hyperoxia or who have been newly diagnosed with pulmonary toxicity.

4. Dosages

The exact amount of the disclosed polypeptide or pharmaceutical composition required can vary from subject to subject, depending on the species, age, weight and general condition of the subject, the severity of the disorder being treated, the particular polypeptide or pharmaceutical composition used, its mode of administration and the like. Thus, it is not possible to specify an exact amount for every composition. However, an appropriate amount can be determined by one of ordinary skill in the art using only routine experimentation. Thus, effective dosages and schedules for administering the polypeptide or pharmaceutical composition may be determined empirically, and making such determinations is within the skill in the art. The dosage ranges for the administration of the polypeptide or pharmaceutical composition are those large enough to produce the desired effect in which the symptoms of disorder are effected. The dosage should not be so large as to cause adverse side effects, such as unwanted cross-reactions, anaphylactic reactions, and the like.

Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the polypeptide or pharmaceutical composition used alone might range from about 1 µg/kg to up to 100 mg/kg of body weight or more per day, depending on the factors mentioned above. Also disclosed are slow release or sustained release system such that a constant dosage is maintained.

B. Screening Methods

1. Identify Small Molecule that Inhibits Association of eNOS with Beta Actin

Also provided is a method of identifying an agent that can be used to prevent lung injury from hyperoxia. The method can involve providing a sample having β-actin, contacting the sample with a candidate agent, and detecting the level of candidate agent/β-actin binding, said detection identifying an agent that can be used to prevent lung injury from hyperoxia. The method can involve providing a sample having eNOS under conditions that allow β-actin and eNOS to bind, contacting the sample with a candidate agent, detecting the level of eNOS/β-actin binding, comparing the binding level to a control, a decrease in eNOS/β-actin binding compared to the control identifying an agent that can be used to prevent lung injury from hyperoxia.

The method can further involve administering the candidate agent to a cell, such as a lung endothelial cell, under hyperoxic conditions and detecting the ability of the candidate agent to prevent oxygen toxicity.

a. Detection of Protein Binding

The binding of candidate agents or eNOS to β-actin can be detected using routine methods, such as immunodetection methods, that do not disturb protein binding. The methods can be cell-based or cell-free assays. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

The binding of candidate agents or eNOS to β-actin can be detected using fluorescence activated cell sorting (FACS). For example, disclosed are cell lines transfected with eNOS and β-actin fused to fluorescent proteins. These cell lines can facilitate high-throughput screens for biologically expressed and small molecule binding to eNOS and β-actin in their physiological forms.

b. Candidate Agents

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that inhibits eNOS binding to β-actin. The described assays for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents include functional groups necessary for structural interaction with proteins, particularly hydrogen bonding, and typically include at least an amine, carbonyl, hydroxyl or carboxyl group, for example, at least two of the functional chemical groups. The candidate agents often include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some embodiments, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the disclosed methods. The libraries can be bacterial, fungal, viral, and vertebrate proteins, and human proteins.

C. Making the Compositions

1. Peptide Fragment Isolation and Purification

The disclosed polypeptide can in some embodiments be produced by cleaving human eNOS or human β-actin into peptide fragments and selecting the fragments having the disclosed polypeptide sequence. As an example, human eNOS can be digested using proteases, and peptide fragments having the β-actin binding domain can be purified from the peptide extract using, for example, antibodies that specifically bind the β-actin binding domain. Thus, also disclosed are antibodies that specifically bind SEQ ID NO:1 and their use in detecting and purifying the disclosed polypeptides.

2. Peptide Synthesis

One method of producing the disclosed polypeptides, such as SEQ ID NOs:1 or 2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method involves of a two step chemical reaction. The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

Alternatively, unprotected peptide segments are chemically linked where the bond formed between the peptide segments as a result of the chemical ligation is an unnatural (non-peptide) bond. This technique has been used to synthesize analogs of protein domains as well as large amounts of relatively pure proteins with full biological activity.

3. Nucleic Acid Synthesis and Recombination

Nucleic acids, such as, the those encoding the disclosed polypeptides, can be made using standard chemical synthesis methods or can be produced using enzymatic methods or any other known method. Such methods can range from standard enzymatic digestion followed by nucleotide fragment isolation to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B).

EXAMPLES

Example 1

An Increase in NO Production Induced by β-Actin Binding to eNOS is Accompanied by a Decrease in Superoxide Formation Materials and Methods
Reagents and Materials Mouse anti-eNOS and anti-Hsp90 antibodies were obtained from Transduction Laboratory (Lexington, Ky.). Anti-β-actin monoclonal antibody was obtained from Sigma. Human β-actin was from Cytoskeleton (Denver, Colo.). $BH_4$ and desferrioxamine was from Calbiochem. Purified Hsp90 was from Stressgen (Ann Arbor, Mich.) and diethyldithiocarbamate was from Alexis Biochemicals (Lausen, Switzerland). NADPH, calmodulin, and other reagents were purchased from Sigma.

eNOS Purification

Recombinant eNOS protein was purified as described previously (Sud, N., et al. (2007) Am. J. Physiol. Lung Cell Mol. Physiol. 293, L1444-53; Rodríguez-Crespo, I., et al. (1996) J. Biol. Chem. 271, 11462-67) with modifications. Briefly, 4 liters of overnight cell culture of human eNOSpCW were used to inoculate 0.5 liters of TB containing ampicillin (50 µg/ml). The cultures were grown to an $A_{600}$ of 0.6 at 22° C. (200 rpm) and induced with 0.5 m isopropyl β-d-l-thiogalactopyranoside (IPTG). One hour before IPTG induction, δ-aminolevulinic acid (0.5 mm final) was added, and at the time of induction riboflavin (3 µm final) and ATP (1 mm final) were also added. After induction, cells were kept in the dark at 22° C. and 200 rpm. After 48 h, cell pellets were collected and frozen in −80° C. until purification. When eNOS protein was purified, the cells were resuspended in buffer A (50 mM Tris-HCl, pH 7.8, 1 mM EDTA, 1 mM DTT, 10% glycerol (v/v), 150 mM NaCl, 0.5 mM L-arginine, 4 µM $BH_4$, 2 µM FAD 0.1 mm phenylmethylsulfonyl fluoride, 1 µM leupeptin, and 1 µM pepstatin), lysed by sonication, and then centrifuged. The supernatant was applied to 2′,5′-ADP Sepharose 4B column equilibrated with buffer B (50 mm Tris-HCl, pH 7.8, 0.1 mm EDTA, 0.1 mm DTT, 150 mM NaCl, 10% glycerol, 0.5 mM L-arginine). The column was washed with 20 volumes of buffer B and again with 20 volumes of buffer B containing 300 mM NaCl. Finally, proteins were eluted with buffer B containing 600 mM NaCl and 5 mM 2′-AMP. Repeated dilution/concentration with buffer containing 40 mM Tris buffer, pH 7.6, containing 1 mM L-arginine, 3 mM DTT, 4 µM $BH_4$, 4 µM FAD, 10% glycerol, and 150 mM NaCl were performed to remove 2′-AMP and to achieve a final concentration of 150 mM NaCl. The DTT, $BH_4$, and FAD were removed, and protein-containing fractions were concentrated using Centricon 50 (Millipore, Billerica, Mass.). The purity of the eNOS protein was verified using SDS-PAGE.

Measurement of NO In Vitro

NO production was determined by measuring $NO_x$ ($NO_2$ and $NO_3$). Purified eNOS and β-actin were preincubated at room temperature for 30 min and then added to a 50-µl reaction mix containing 50 mM HEPES buffer, 1 mM NADPH, 100 µmM Larginine, 1 mmM $CaCl_2$, 10 µg/ml calmodulin, 4 µM $BH_4$. The mixture was incubated at 37° C. for 30 min. 40 µl of the reaction mix were loaded to the SIEVERS machine for $NO_x$ measurement according to standard manufacturer's instructions as previously described (Church, J. E., and Fulton, D. (2006) J. Biol. Chem. 281, 1477-88). For experiments with ABS peptides, β-actin and peptides were preincubated at room temperature for 20 min before eNOS protein was added.

Detection of Superoxide Generation In Vitro eNOS-derived superoxide generation was measured by electron paramagnetic resonance (EPR) spectroscopy and spin trapping as previously described (Sud, N., et al. (2008) Am. J. Physiol. Cell Physiol. 294, C1407-18). 50 µl of reaction mix containing 50 mM HEPES buffer, 1 mM NADPH, 100 µM Larginine, 1 mM $CaCl_2$, 10 µg/ml calmodulin, and 1 µg of purified eNOS were incubated at 37° C. for 60 min. 12.5 µl of spin probe N1-hydroxy-3-methoxy-carbonyl-2,2,5,5-tetramethyl-pyrrolidine (CMH) in EPR buffer were added to the reaction mix. 35 µl of the final reaction mix were loaded into a 50-µl capillary tube and analyzed with a MiniScopeMS200 EPR (Magnetech, Berlin, Germany). A reaction curve was generated by adding 1 unit/ml of xanthine oxidase into 500 µM xanthine solution in buffered PBS (pH 7.4), which contains 5 µM diethyldithiocarbamate and 25 µMm desferrioxamine to inhibit any conversion of superoxide into either hydrogen peroxide or hydroxyl radical via Fenton reaction. Reactions were allowed to proceed at 25° C. for up to 40 min. Following incubation, ~35 µl of each reaction mixture was loaded into a 50 µl capillary tube and analyzed immediately with EPR spectroscopy. EPR spectra were analyzed for amplitude using ANALYSIS software (version 2.02, Magnettech). Given that 1 unit of xanthine oxidase will convert 1 µmol of xanthine per minute at 25° C., based on this standard curve, it was calculated that 1 EPR amplitude units is equivalent of 0.35 pmol of superoxide.

Results

β-actin-binding site on eNOS protein is located at the oxygenase domain (Su, Y., Kondrikov, D., and Block, E. R. (2007) Sci. STKE 2007, e52-1-e52-3; Kondrikov, D., et al. (2006) Am. J. Physiol. Lung Cell Mol. Physiol. 290, L41-50). The oxygenase domain is involved with superoxide generation when eNOS is uncoupled because of limited BH4 availability (Va'squez-Vivar, J., et al. (1998) Proc. Natl. Acad. Sci. U.S.A. 95, 9220-25; Xia, Y., et al. (1998) J. Biol. Chem. 273, 25804-08). To test whether β-actin association with eNOS modulates the formation of superoxide, superoxide and NO production by purified eNOS was measured using EPR spectrometry in the absence and the presence of G-actin.

Figure 1B:
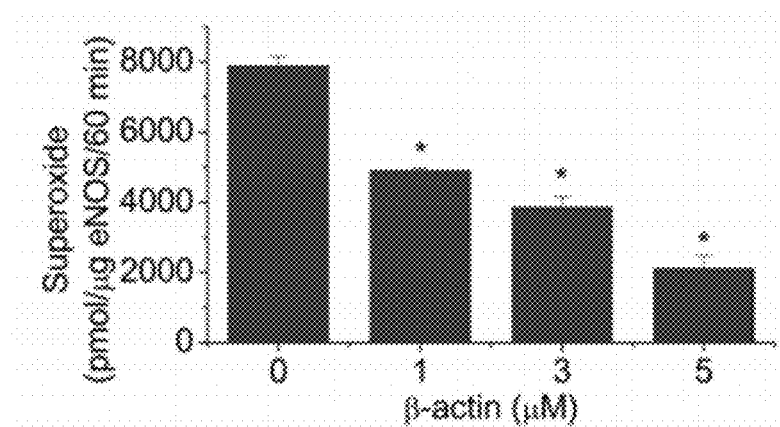
FIG. 1B is a bar graph showing superoxide production (pg/μg eNOS/60 min) as a function of β-actin at 0, 1, 3, and 5 μM.
Figure 1C:
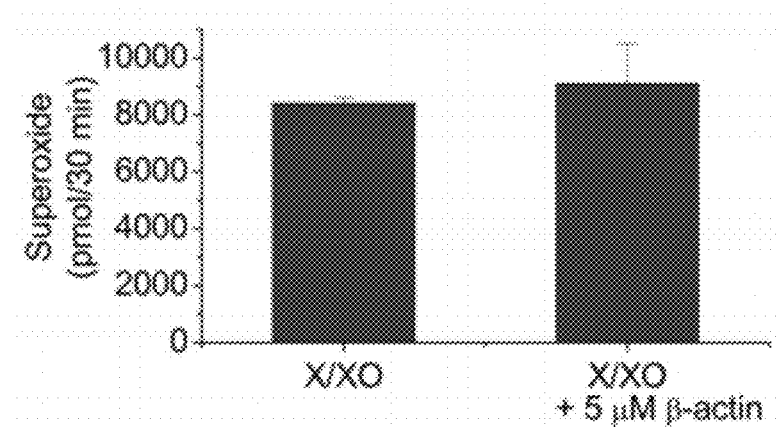
FIG. 1C is a bar graph illustrating superoxide production (pmol/30 min) as a function of xanthine oxidase (1.0 u) and 500 μm xanthine in 500 μl of PBS (pH 7.4), which contains 5 μm diethyldithiocarbamate and 25 μm desferrioxamine to inhibit any conversion of superoxide into either hydrogen peroxide or hydroxyl radical, in the absence and presence of 5 μm β-actin. Results are expressed as mean±S.E.; n=3 experiments. *p<0.05 versus control.

FIGS. 1A-1C are bar graphs showing β-actin increases NO production and decreases superoxide formation from eNOS. Purified eNOS and β-actin were incubated at room temperature for 30 min before being added to 50 µl reaction mix for NOx ($NO_2$ and $NO_3$) measurement using the SIEVERS machine (FIG. 1A) and for superoxide analysis using EPR spectroscopy and spin trapping (FIG. 1B).

As shown in FIG. 1A, incubation of purified eNOS with β-actin caused an increase in NO production in a dose-dependent manner. However, the level of superoxide produced by eNOS is decreased in the presence of β-actin (1-5 µm) (FIG. 1B). β-Actin did not affect the level of superoxide generated from xanthine oxidase (FIG. 1C), indicating that β-actin does not scavenge superoxide. These data indicate that β-actin binding to eNOS prevents superoxide generation from eNOS and shifts the enzymatic activity from forming superoxide toward NO production.

Example 2

Figures 2A, 2B:
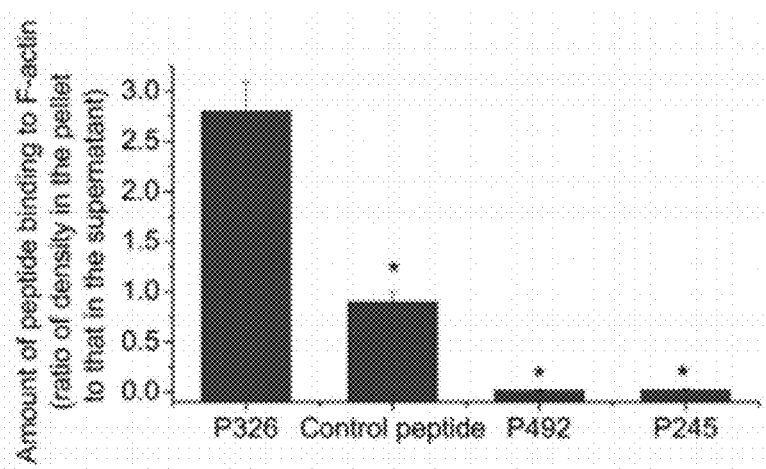
FIG. 2A is a sequence alignment of the three putative actin-binding sequences (ABS) to actin-binding proteins. The highlight indicates same or similar amino acids. Shown are ABS 245 (SEQ ID NO:3), human dystrophin aa 88-116 (NVDLVNIGST DIVDGNHKLT LGLIWNIIL; SEQ ID NO:4), human plectin aa 251-279 (QVKLVNIRDD DIADGNPKLT LGLIWTIIL; SEQ ID NO:5), human β-spectrin aa 127-155 (RVHLENMGSH DIVDGNHRLV LGLIWTIIL; SEQ ID NO:6), ABS 326 (SEQ ID NO:1), human dystrophin aa 108-115 (LGLIWNII; SEQ ID NO:7), human plectin aa 271-278 (LGLLWTII; SEQ ID NO:8), human β-spectrin aa 147-154 (LGLIWYII; SEQ ID NO:9), ABS 492 (RKKTFKEVANA; SEQ ID NO:10), human dystrophin aa 17-27 (QKKTFTKWVNA; SEQ ID NO:11), human plectin aa 181-191 (QKKTFTKWVNK; SEQ ID NO:12), human β-spectrin aa 56-66 (QKKTFTKWVNS; SEQ ID NO:13).
FIG. 2B is a bar graph depicting from left to right the amount of P326, control peptide, P492, and P245 binding to F-actin expressed as the ratio of peptide density in the pellet to that in the supernatant. Results are expressed as mean±S.E.; n=3 experiments. *p<0.05 versus P326.

Sequence Comparison of eNOS and Several Actin-binding Proteins Containing the Calponin Homology (CH-1) Domain The actin-binding region of eNOS is in the oxygenase domain of eNOS protein based on data from the yeast two-hybrid experiments (Kondrikov, D., et al. (2006) Am. J. Physiol. Lung Cell Mol. Physiol. 290, L41-50). Using the program VECTOR NTI, a sequence alignment analysis was made of sequences of eNOS protein against the CH-1 domain, an actin-binding region of the calponin homology domain in a number of signaling and actin cross-linking molecules i.e. α-actinin, dystrophin, and utrophin. Three regions in the eNOS oxygenase domain were found to have high consensus with ABSs in these actin-binding proteins (FIG. 2a). These ABSs are actin-binding motifs (Keep, N.H. (2000) Neurol. Sci. 21, S929-37; Garcia'-Alvarez, B., et al. (2003) Structure 11, 615-25).

Example 3

Binding of ABS Peptides to β-Actin and Their Effect on eNOS-β-Actin Association Materials and Methods
Synthesis of ABS Peptides
To study the function of three putative ABSs of eNOS, peptides corresponding to the amino acid sequences of these three putative ABSs were synthesized by GeneScript Corporation (Piscataway, N.J.). A modified version of ABS peptide 326 with hydrophobic leucine and tryptophan substituted for neutrally charged alanine was used as a control peptide for ABS peptide 326. The amino acid sequences of the peptides are NSQLVRYAGYRQQDGSVRGDPANVEITEL (SEQ ID NO:3) for ABS peptide 245, RKKTFKEVANA (SEQ ID NO:10) for ABS peptide 492, LGLRWYAL (SEQ ID NO:1) for ABS peptide 326, AGARAYAA (SEQ ID NO:44) for control peptide for ABS peptide 326, RKKRRQRRRALGL-RWYAL (SEQ ID NO:2) for ABS peptide 326 TAT (P326TAT), and RKKRRQRRRAAGARAYAA (SEQ ID NO:14) for control peptide TAT.

Assay of Peptide Binding to β-Actin

The binding capacities of the peptides to β-actin were measured by using an F-actin binding spin-down assay kit from Cytoskeleton, Inc. (Denver, Co). Monomeric human β-actin was polymerized into F-actin in F-actin buffer (5 mM Tris-HCl, pH 7.8, 1 mM ATP, 0.5 mM DTT, 0.2 mmM $CaCl_2$, 0.2 mM $MgCl_2$, and 100 mM KCl) for 1 h at 24° C. ABS peptides at final concentrations of 10 μM were incubated alone or with 23 μM F-actin in F-actin buffer for 30 min in a total volume of 50 μl. The mixtures were centrifuged at 150,000×g for 2 h at 24° C. in a Beckman TLA-100 rotor. Supernatant and pellet fractions were resuspended in loading buffer and subjected to SDS-PAGE. The gel was stained with Coomassie Blue. The density of the band was measured using Software Image J.

Results

Actin binding capabilities of the synthesized ABS peptides corresponding to putative ABSs in eNOS were evaluated by the F-actin binding spin-down assay. ABS peptides 326 (P326), control peptides, ABS peptides 492 (P492), and ABS peptides 245 (P245) at final concentrations of 10 μm were incubated for 30 min alone or with 23 μm F-actin in F-actin buffer containing 2.5 μM ATP and 2.5 μM DTT. After high speed centrifugation at 150,000×g for 2 h, the supernatants and pellets were subjected to SDS-PAGE analysis.

As shown in FIG. 2b, F-actin was pulled down to the pellets by high-speed centrifugation. In the absence of F-actin, ABS peptides remained in the supernatant fraction. However, in the presence of F-actin, a significant portion of peptide 326 was pulled down to the pellets with F-actin. Only a very small amount of the control peptide for peptide 326 was pulled down to the pellets with F-actin. Peptides 492 and 245 were not pulled down to the pellets with F-actin. These results indicate that ABS peptide 326, which is a sequence from the eNOS oxygenase domain, can specifically bind to β-actin.

To further study whether ABS peptide 326 can competitively affect eNOS-β-actin association, purified G-actin was incubated with purified recombinant eNOS protein in the presence of ABS peptide 326 or its control peptide. Then eNOS protein was precipitated using protein G-agarose conjugated with eNOS monoclonal antibody. The amounts of eNOS and β-actin protein in the pellets were measured using Western blot analysis.

Figure 3:
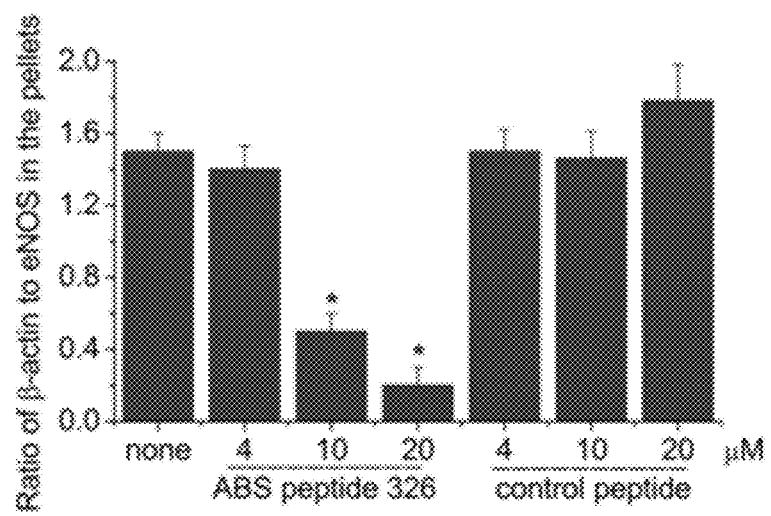
FIG. 3 is a bar graph showing the ratio of eNOS and β-actin in anti-eNOS immunoprecipitated pellets as a function of ABS peptide 326 (0, 4, 10, and 20 μM) or control peptide (4, 10, and 20 μM) incubation at room temperature for 30 min. Results are expressed as mean±S.E.; n=3 experiments. *, p<0.05 versus control peptide.

As shown in FIG. 3, β-actin can be pulled down to the pellets together with eNOS. ABS peptide 326 decreased the amount of β-actin precipitated with eNOS protein in a dose-dependent manner. In contrast, the control peptide for peptide 326, in which residues leucine 326, leucine 328, tryptophan 330, and leucine 333 were replaced by alanine, in the same concentrations did not affect the amount of β-actin precipitated with eNOS protein. Taken together, these data show that ABS peptide 326 specifically binds to β-actin and competitively inhibits eNOS-β-actin association.

Example 4

ABS Peptide 326 Prevents β-Actin-induced Increase in NO and L-Citrulline Production and Decrease in Superoxide Formation In Vitro Results To study whether competitive inhibition of eNOS-β-actin association by ABS peptide 326 prevents β-actin-induced increase in NO and L-citrulline production and decrease in superoxide production from eNOS, β-actin-induced production of NO, L-citrulline, and superoxide were analyzed in the absence and presence of ABS peptide 326 and its control peptide.

Figure 4A:
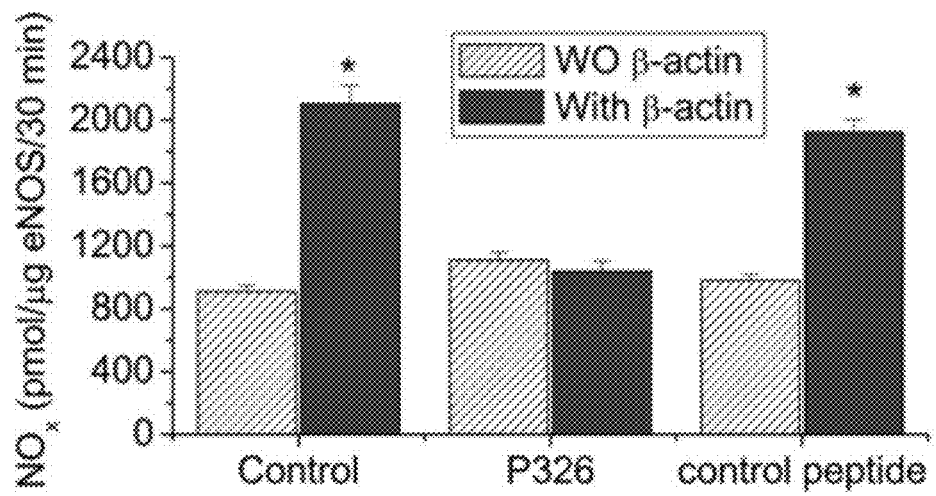
FIG. 4A is a bar graph showing $NO_x$ ($NO_2$ and $NO_3$) production (pg/μg eNOS/30 min) as a function of eNOS incubation with nothing (first two bars), P326 (second two bars), or control peptide (third two bars) each with β-actin (left bar) or without β-actin (right bar).
Figure 4B:
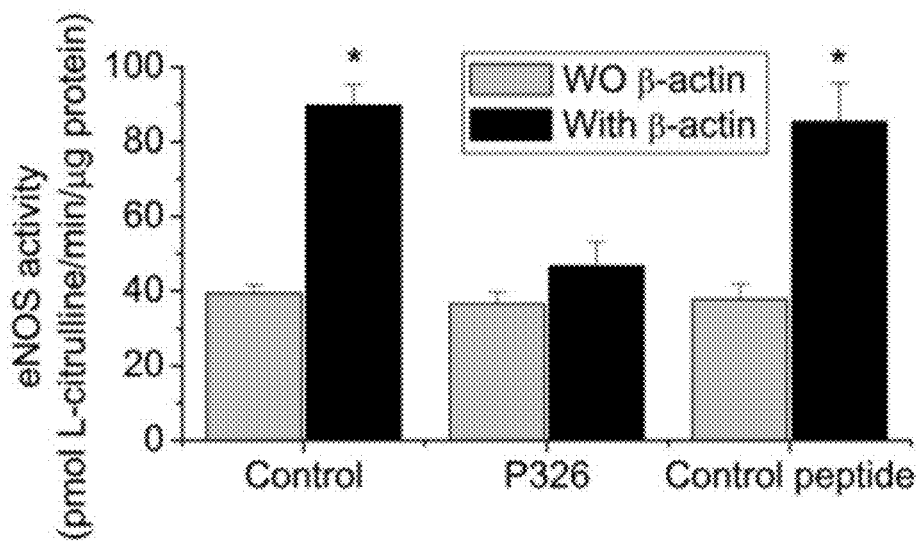
FIG. 4B is a bar graph showing L-citrulline production (pmol/min/μg protein) as a function of eNOS incubation with nothing (first two bars), P326 (second two bars), or control peptide (third two bars) each with β-actin (left bar) or without β-actin (right bar).
Figure 4C:
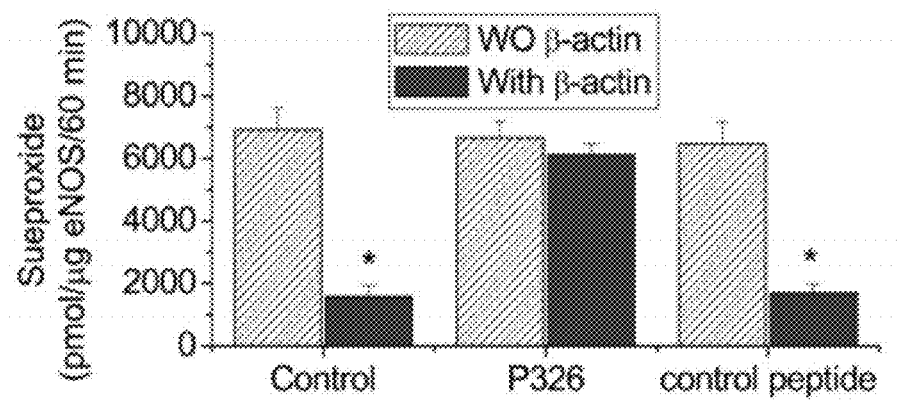
FIG. 4C is a bar graph showing superoxide production (pg/μg eNOS/60 min) as a function of eNOS incubation with nothing (first two bars), P326 (second two bars), or control peptide (third two bars) each with β-actin (left bar) or without β-actin (right bar).
Figure 4D:
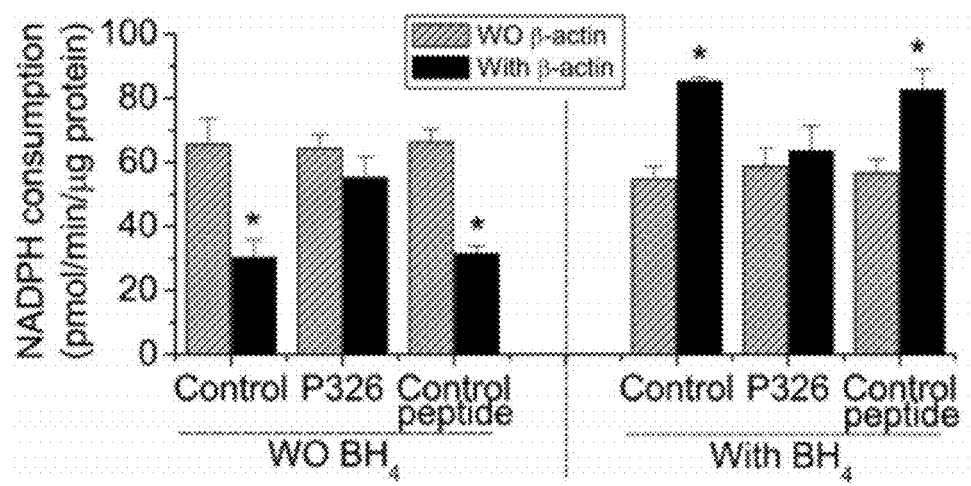
FIG. 4D is a bar graph showing NADPH consumption (pmol/min/μg protein) as a function of eNOS incubation with nothing (first two bars), P326 (second two bars), or control peptide (third two bars) each with β-actin (left bar) or without β-actin (right bar) either with $BH_4$ (right set of bars) or without $BH_4$ (left set of bars). Results are expressed as mean±S.E.; n=3 experiments. *, p<0.05 versus without β-actin (WO β-actin).

Purified eNOS (1.0 μg/500 μl) and β-actin (2.0 μm) were incubated at room temperature in the presence of ABS peptide 326 (P326) or its control peptide (20 μm) for 30 min before being added to 50 μl of master mix for NO measurement using the SIEVERS machine (FIG. 4a), L-citrulline assay (FIG. 4B), superoxide analysis using spin-trapping EPR spectroscopy (FIG. 4c), and NADPH consumption assay with or without $BH_4$ (FIG. 4D).

ABS peptide 326 per se did not affect NO and L-citrulline production and superoxide formation (FIG. 4A-4C), indicating that peptide 326 does not scavenge NO or superoxide. Moreover, ABS peptide 326 prevented β-actin-induced increase in NO and L-citrulline production (FIGS. 4A and 4B) and decrease in superoxide formation (FIG. 4C). However, control peptide in which residues leucine 326, leucine 328, tryptophan 330, and leucine 333 were replaced by alanine did not affect β-actin-induced changes in the production of NO, L-citrulline, and superoxide from eNOS (FIG. 4a-4c). In addition, incubation of purified eNOS with purified G-actin resulted in a decrease in NADPH consumption in absence of $BH_4$ and ABS peptide 326 prevented β-actin-induced decrease in NADPH consumption (FIG. 4d). Taken together, these data indicate that ABS peptide 326 specifically binds to β-actin and blocks the effects of β-actin on the production of NO, L-citrulline, and superoxide from eNOS.

Example 5

Mutation of Residues Leucine 326, Leucine 328, Tryptophan 330, and Leucine 333 for Alanine Decreases eNOS-β-Actin Association and NO Production and Increases Superoxide Generation Materials and Methods Site-Directed Mutagenesis of eNOS and Transfection of COS-7 Cells with Wild Type and eNOS Mutant Human eNOS gene (GenBank™ M93718.1) was cloned into HindIII and XbaI sites of pcDNA3 vector and regarded as wild-type eNOS. The cDNA of human eNOS was mutated to substitute residues leucine 326, leucine 328, tryptophan 330, and leucine 333 for alanine in the actin-binding site. The site-directed mutagenesis was custom-made by Retrogen (San Diego, Calif.). The sequences of both strands of the gene in the mutated region were verified by using ABI 3730 automated sequencer. Plasmids containing wild-type eNOS cDNA or eNOS mutant cDNA were transfected into COS-7 cells using Lipofectamine LTX with PLUS reagent (Invitrogen, Carlsbad, Calif.) according to the manufacturer's protocol. 48 h after transfection, cells were used for co-immunoprecipitation and assays for NO and superoxide generation.

Co-Immunoprecipitation

Wild-type and eNOS mutant-transfected COS-7 cells were washed in ice-cold PBS and lysed in Tris buffer (50 mM Tris, pH 7.4, 10 mM NaF, 2.5 mM EDTA, 15 mM $Na_2P_2O_7$, 1% Triton X-100, and 1× protease inhibitor mixture). The lysates or mixtures of eNOS and β-actin were incubated with anti-eNOS antibody at 4° C. overnight. 30 µl of protein A-Sepharose were added, and samples were further incubated for 2 h at 4° C. Immunoprecipitates were collected by centrifugation and washed three times in buffer containing 50 mm Tris-HCl, pH 7.5, 150 mm NaCl, and 0.1% Triton X-100. Proteins were eluted from Sepharose beads by boiling the samples in 30 µl of SDS immunoblotting sample buffer. Sepharose beads were pelleted by centrifugation at 10,000×g, and supernatants were analyzed for eNOS and β-actin by Western blotting.

Determination of NO Production and Superoxide Formation in COS-7 Cells

After wild-type and eNOS mutant transfection, ionomycin (2 µm) was added to the cells. After 30 min of incubation, culture medium was collected and ethanol-precipitated to remove proteins. 50 µl of the reaction mix were loaded to the SIEVERS machine for $NO_x$ measurement according to standard manufacturer's instructions (Church, J. E., and Fulton, D. (2006) J. Biol. Chem. 281, 1477-88). In some experiments, $N^G$-nitro-1-arginine methyl ester ($_L$-NAME), a specific eNOS inhibitor, was used to inhibit NO production. The results indicate that incubation of endothelial cells with 1-NAME resulted in a 90% inhibition of NO production, suggesting that this method is reliable to detect NO production. For superoxide assay, after incubation with ABS peptides, the spin trap CMH was added to the cells. Superoxide from cells was trapped for 1 h, and then cells were scraped and subjected to EPR spectroscopy as previously described (Sud, N., et al. (2008) Am. J. Physiol. Cell Physiol. 294, C1407-18). Protein contents in the cell lysates were determined by Lowry's method.

Determination of Catalytic Activity, NADPH Consumption, and Superoxide Generation from Purified eNOS Mutant Wild-type and mutant eNOS proteins in COS-7 cells were purified. The catalytic activity of purified eNOS mutant protein was assayed by the measurement ofl-[$^3$H]citrulline formation from 1-[$^3$H]arginine as reported previously (Su, Y., et al. (2003) Am. J. Physiol. Cell Physiol. 284, C1542-49). To determine NADPH consumption by eNOS, 0.3 mm NADPH was added to 200 µl of reaction mix containing 1 µg eNOS, 1 µM FAD, 1 µmM FMN, 10 µg/ml calmodulin, 100 µMm L-arginine, 1 mM $CaCl_2$, 10 µg/ml calmodulin, and 2.5 mM ATP. The reaction was monitored at 340 mM for 10 min. NADPH consumption was calculated by using a molar extinction coefficient 6.22 mm$^-$·cm$^{-1}$. The superoxide formation from purified eNOS mutant was measured by spin trapping and EPR spectroscopy.

Results

Figure 5A:
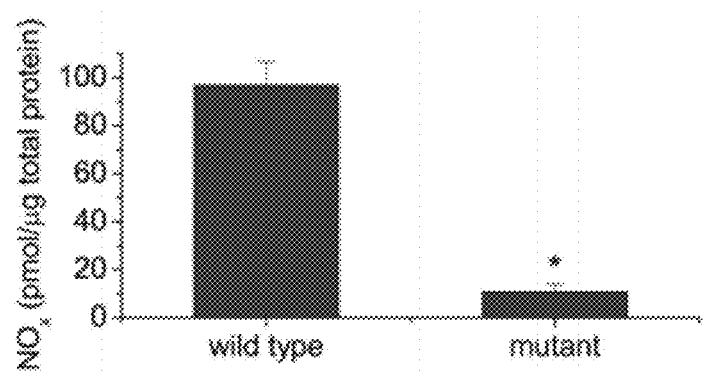
FIG. 5A is a bar graph showing $NO_x$ ($NO_2$ and $NO_3$) production (pmol/μg total protein) in COS-7 cells transfected with wild type (left bar) and mutant (right bar) eNOS plasmids.
Figure 5B:
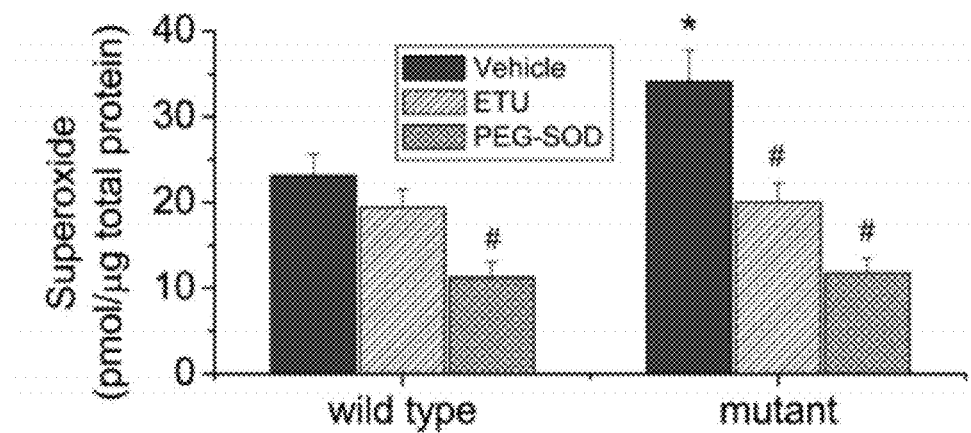
FIG. 5B is a bar graph showing superoxide production (pmol/μg total protein) in COS-7 cells transfected with wild type (left set of bars) and mutant (right set of bars) eNOS plasmids and incubated in the presence of vehicle (left bars), 2-ethyl-2-thiopseudourea (ETU) (middle bars), or PEG-SOD (right bars). Results are expressed as mean±S.E.; n=3 experiments. *, p<0.05 versus wild-type group. #, p<0.05 versus vehicle group.

The control peptide for peptide 326 in which hydrophobic leucine and tryptophan were replaced by neutrally charged alanine had much lower capacity to bind β-actin (FIG. 2) and did not affect eNOS-β-actin association (FIG. 3) and β-actin-induced changes in NO and superoxide production from eNOS in vitro (FIG. 4), indicating that hydrophobic leucine and tryptophan in the actin-binding site might be critical for eNOS-β-actin interaction. To further confirm that role of these residues in eNOS-β-actin association, residues leucine 326, leucine 328, tryptophan 330, and leucine 333 were replaced for alanine by site-directed mutagenesis. The plasmids containing wild type and mutant eNOS genes were transfected into COS-7 cells and then eNOS-β-actin association were measured using co-immunoprecipitation The amount of β-actin co-precipitated with eNOS mutant was much smaller than that with wild-type eNOS, and the eNOS protein levels were similar. COS-7 cells with mutant eNOS exhibited much lower NO production and higher superoxide generation (FIGS. 5A and 5B). In the presence of a specific NOS inhibitor 2-ethyl-2-thiopseudourea (ETU, 100 µm) (Sud, N., et al. (2007) Am. J. Physiol. Lung Cell Mol. Physiol. 293, L1444-53; Lakshminrusimha, S., et al. (2007) Am. J. Physiol. Heart Circ. Physiol 293, H1491-97) or PEG-SOD, the amounts of superoxide generated from COS-7 cells containing wild type and eNOS mutant were comparable (FIG. 5B), indicating that increased superoxide generation is from expressed eNOS in COS-7 cells.

Figure 6A:
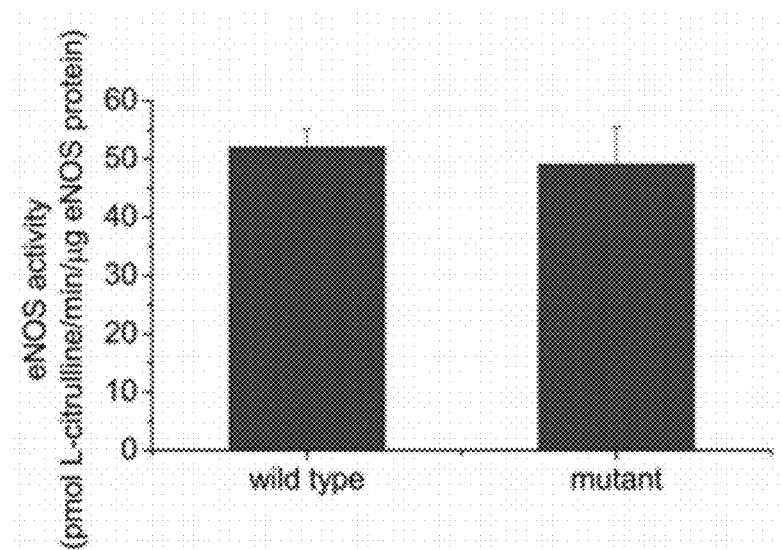
FIG. 6A is a bar graph showing L-citrulline production (pmol/min/μg eNOS protein) in COS-7 cells transfected with wild type (left bar) and mutant (right bar) eNOS plasmids.
Figure 6B:
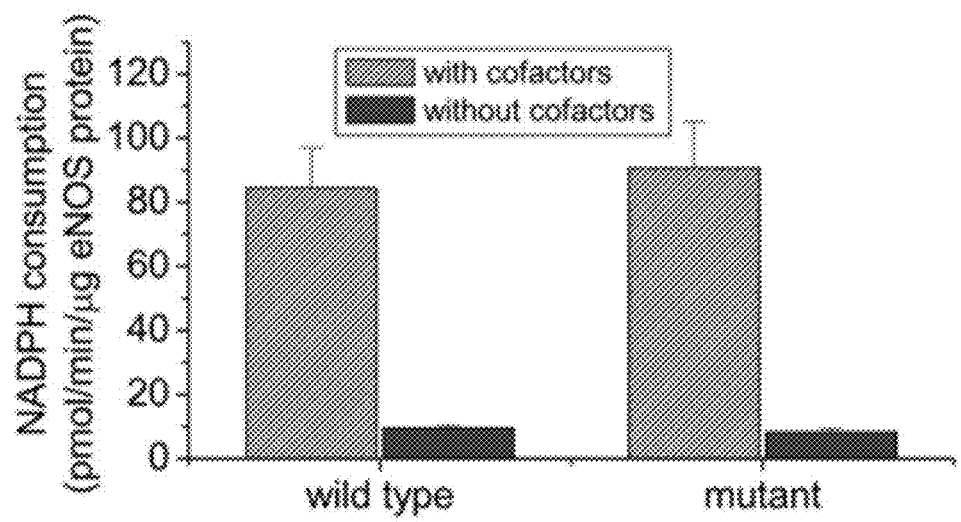
FIG. 6B is a bar graph showing NADPH consumption (pmol/min/μg eNOS protein) in COS-7 cells transfected with wild type (left set of bars) and mutant (right set of bars) eNOS plasmids incubated either with cofactors (left bars) or without cofactors (right bars).
Figure 6C:
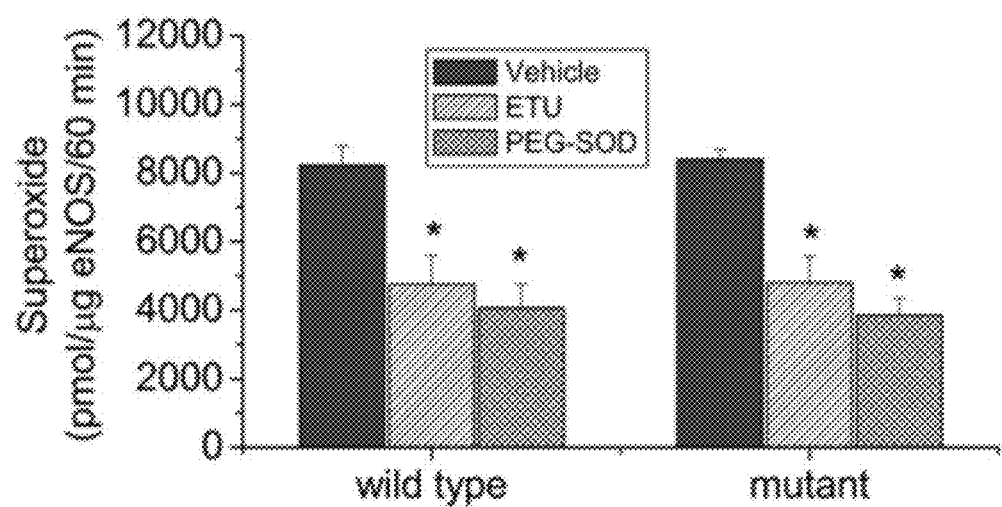
FIG. 6C is a bar graph showing superoxide production (pmol/μg eNOS/60 min) in COS-7 cells transfected with wild type (left set of bars) and mutant (right set of bars) eNOS plasmids and incubated in the presence of vehicle (left bars), ETU (middle bars), or PEG-SOD (right bars). Results are expressed as mean±S.E.; n=3 experiments. *, p<0.05 versus vehicle group.

To exclude the possibility that mutation of residues leucine 326, leucine 328, tryptophan 330, and leucine 333 directly causes the alterations in NO and superoxide generation in COS-7 cells, wild-type and mutated eNOS expressed in COS-7 cells were purified. It was found that the catalytic activity and rate of NADPH consumption and superoxide generation from purified wild-type and mutated eNOS were comparable (FIG. 6A-6C). These data indicate that a decrease in NO production and an increase in superoxide generation in the eNOS mutant are not caused by the direct effect of the mutation.

Example 6

ABS Peptide 326 Decreases eNOS-β-Actin Interaction and NO Production and Increases Superoxide Formation in Intact Endothelial Cells Materials and Methods Transfection of Endothelial Cells with ABS Peptides Pulmonary artery endothelial cells were incubated with ABS peptides at 20 µm final concentration in MEM medium. After 1 h of initial transfection, RPMI medium containing 4% fetal bovine serum (FBS) was added to reach final concentration of 2% FBS. Cells were then incubated for another 2 h before being used for co-immunoprecipitation and eNOS activity assays.

Determination of eNOS-β-Actin Association, NO Production, and Superoxide Formation in Endothelial Cells eNOS-β-Actin association was evaluated using co-immunoprecipitation.

To measure NO production, endothelial cells were incubated with ABS peptides for 3 h. Then ionomycin (2 µM) was added to the cells. After an additional 30 min, culture medium was collected and ethanol-precipitated to remove proteins. 50 µl of the reaction mix were loaded to the SIEVERS machine for $NO_x$ measurement as described above. For superoxide assay, after incubation with ABS peptides, the spin trap CMH was added to the cells. Superoxide from cells was trapped for 1 h, and then cells were scraped and subjected to EPR spectroscopy.

Results

ABS peptide 326 specifically binds to β-actin and competitively inhibits eNOS-β-actin association in vitro. To study whether ABS peptide 326 affects eNOS-β-actin association in intact endothelial cells, pulmonary artery endothelial cells were transfected with ABS peptide 326 linked to an 11-amino acid transduction domain of HIV TAT (P326TAT) as described by Gustafsson et al. (Gustafsson, A. B., et al. (2005) Methods Mol. Med. 112, 81-90). This TAT tag is a novel method used to facilitate delivery of biologically active proteins or peptides into cells and tissues through the fusion of a protein transduction domain to the protein or peptide of interest (Gustafsson, A. B., et al. (2002) Circulation 106, 735-39). To confirm the efficiency of P326TAT and control peptide TAT to enter endothelial cells, FITC-labeled P326TAT and FITC-labeled control peptide TAT were used. Incubation of endothelial cells with FITC-labeled P326TAT and FITC-labeled control peptide TAT (20 μm) for 3 h resulted in marked fluorescence accumulation in endothelial cells, indicating that P326TAT and control peptide TAT can enter endothelial cells efficiently. Endothelial cells were incubated with P326TAT and control peptide TAT for 3 h, and then eNOS-β-actin association was evaluated by co-immunoprecipitation using anti-eNOS antibody.

Figure 7A:
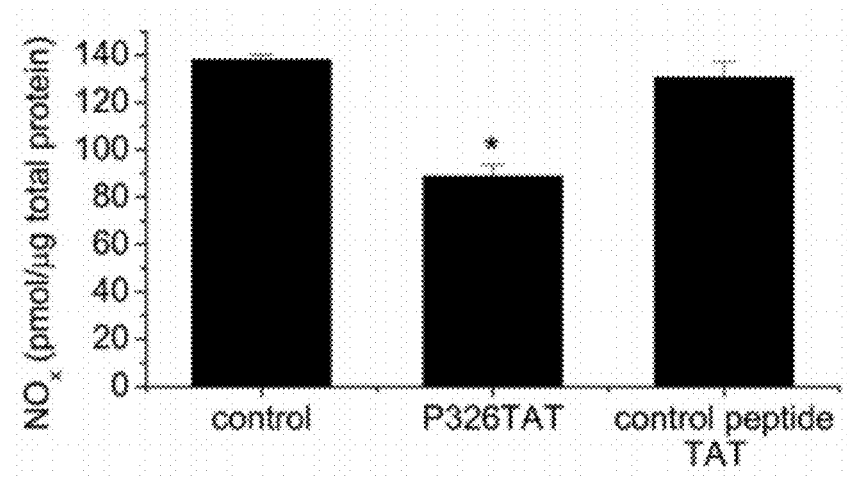
FIG. 7A is a bar graph showing $NO_x$ ($NO_2$ and $NO_3$) production (pmol/µg total protein) in pulmonary artery endothelial cells incubated with nothing (left bar), P326TAT (middle bar), or control peptide TAT (right bar).
Figure 7B:
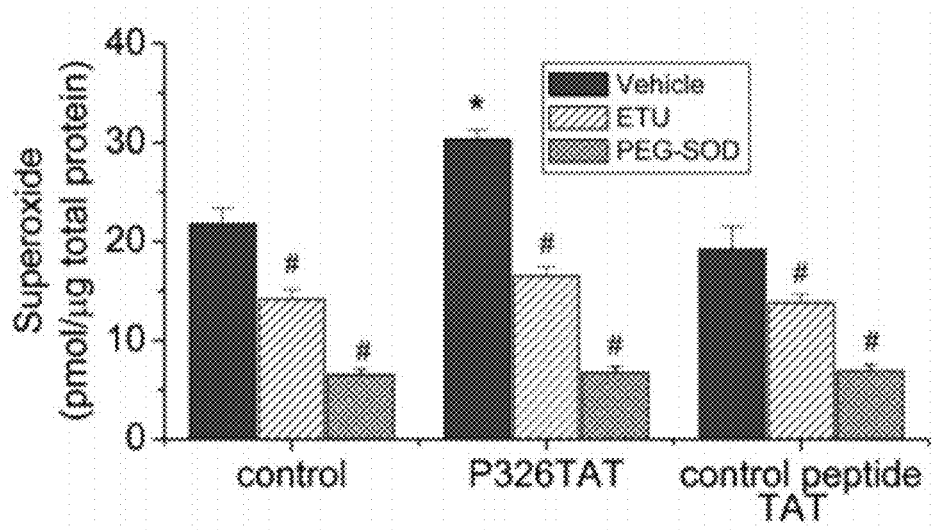
FIG. 7B is a bar graph showing superoxide production (pmol/µg total protein) in pulmonary artery endothelial cells incubated with nothing (left set of bars), P326TAT (middle set of bars), or control peptide TAT (right set of bars) and incubated in the presence of vehicle (left bars), ETU (middle bars), or PEG-SOD (right bars).

Transfection of endothelial cells with P326TAT significantly decreased the amount of β-actin co-immunoprecipitated with eNOS. NO and superoxide production was then measured in P326TAT-transfected endothelial cells. As shown in FIG. 7a, transfection of endothelial cells with P326TAT significantly decreased NO production without any alteration in eNOS protein content and in eNOS protein localization in endothelial cells. Meanwhile, superoxide formation was much higher in P326TAT-transfected endothelial cells than control peptide TAT-transfected endothelial cells (FIG. 7b). The specific NOS inhibitor ETU (100 μm) (Lakshminrusimha, S., et al. (2007) Am. J. Physiol. Heart Circ. Physiol 293, H1491-97) inhibited P326TAT-induced increase in superoxide formation (FIG. 7b), indicating that the increased superoxide generation was from eNOS rather than mitochondria or xanthine oxidase. Taken together, these results indicate that ABS peptide 326 prevents eNOS-β-actin association, reduces NO production, and increases superoxide formation in intact endothelial cells.

Example 7

ABS Peptide 326 Did Not Affect eNOS-Hsp90 Interaction in Endothelial Cells

To rule out the possibility that the effect of P326TAT on eNOS activity in endothelial cells is caused by its effect on eNOS-Hsp90 interaction, eNOS-Hsp90 association was measured by co-immunoprecipitation using eNOS antibody. The amount of Hsp90 co-precipitated with eNOS protein was comparable between P326TAT-transfected cells and control peptide TAT-transfected cells, indicating that P326TAT did not affect eNOS-Hsp90 interaction and that P326TAT-induced inhibition of eNOS activity was not caused by alteration in eNOS-Hsp90 interaction.

Example 8

ABS Peptide 326 Decreases Endothelial Wound Repair

Materials and Methods

Endothelial Monolayer Wound Repair

Pulmonary artery endothelial cells were incubated with ABS peptides for 3 h. Then endothelial monolayer wound repair in the absence and presence of PEG-SOD (100 units/ml) and NOC-18 (10 μm) was measured as previously reported (Su, Y., et al. (2006) FASEB J. 20, 1443-51). Endothelial monolayer wound repair distance was expressed as the width of the wound before treatment subtracted by that after treatment.

Statistical Analysis

In each experiment, experimental and control cells were matched for cell line, age, seeding density, number of passages, and number of days postconfluence to avoid variation in tissue culture factors that can influence measurements of NO and superoxide production. Results are shown as means±S.E. for n experiments. Student's paired t test was used to determine the significance of differences between the means of experimental and control cells. A value of $p<0.05$ was taken as significant.

Results

Figure 7C:
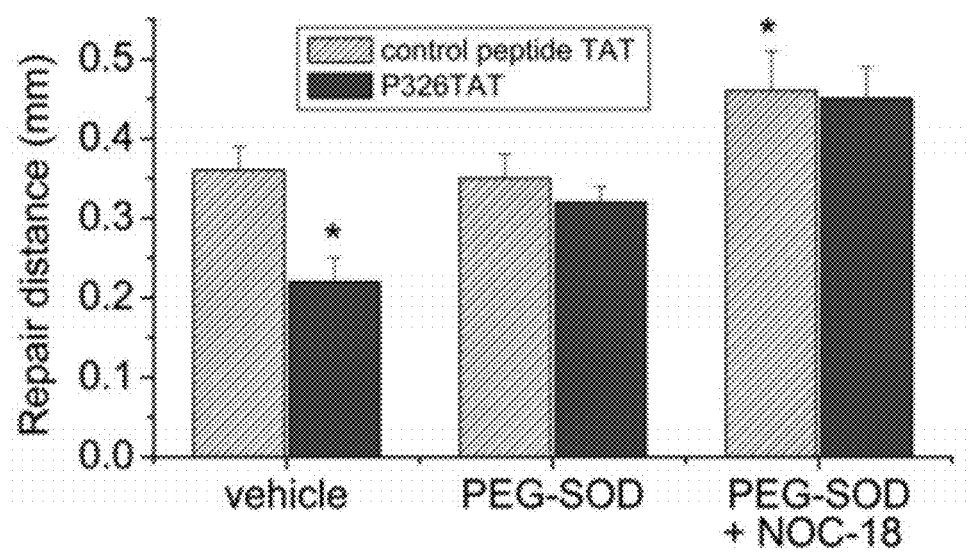
FIG. 7C is a bar graph showing repair distance (mm) of endothelial monolayers incubated with vehicle, PEG-SOD (left set of bars), or PEG-SOD (middle set of bars) and NOC-18 (right set of bars) and incubated with control peptide (left bars) or P326TAT (right bars). Results are expressed as mean±S.E.; n=4 experiments. *, p<0.05 versus control peptide; #, p<0.05 versus vehicle.

To investigate whether P326TAT-induced alterations in eNOS-β-actin interaction and in NO and superoxide generation from eNOS result in functional changes in endothelial cells, endothelial monolayer wound repair was evaluated in endothelial cells incubated with P326TAT and its control peptide. As shown in FIG. 7c, endothelial monolayer incubated with P326TAT (20 μm) exhibited lower capacity of wound repair and PEG-SOD and NOC-18 prevented P326TAT-induced decrease in monolayer wound repair.

Example 9

Hyperoxia Increases the Formation of Peroxynitrite and Superoxide in PAEC

Materials and Methods

Reagents and Materials

Mouse anti-eNOS and anti-Hsp90 antibodies were obtained from Transduction Laboratory (Lexington, Ky.). Anti-β-actin monoclonal antibody was obtained from Sigma. Antibodies against eNOS phosphorylated at serine 1177 and threonine 495 were from Cell Signaling Technology (Denvers, Mass.). nNOS antibody was from Millipore. iNOS antibody was from BD Transduction. β-Actin siRNA was from Ambion (Austin, Tex.). Anti-nitrotyrosine antibody is from Cayman Chemical (Ann Arbor, Mich.). Aminophenyl fluorescein (APF) was from Enzo Life Sciences International (Farmingdale, N.Y.). Other reagents were purchased from Sigma.

Cell Culture and Hyperoxic Exposure

Endothelial cells (PAEC) were obtained from the main pulmonary artery of 6-7-month-old pigs and were cultured as previously reported (Su, Y., et al. (1998) Am. J. Respir. Cell Mol. Biol. 19, 819-825). Third- to sixth-passage cells in monolayer culture were maintained in RPMI 1640 medium containing 4% fetal bovine serum and antibiotics (10 units/ml penicillin, 100 μg/ml streptomycin, 20 μg/ml gentamicin, and 2 μg/ml Fungizone) and were used 2 or 3 days after confluence. For hyperoxic exposure, the confluent monolayers of PAEC were incubated at 37° C. to 95% $O_2$-5% $CO_2$ (hyperoxia) or air-5% $CO_2$ (normoxia) at 1 atmosphere for 1-24 h.

Measurement of Peroxynitrite and Protein Tyrosine Nitration

Peroxynitrite was measured as described by Saito et al. (Saito, S., et al. (2006) Plant Cell Physiol. 47, 689-697). Briefly, after hyperoxic exposure, endothelial cells were washed with warmed modified Hank's balanced salt solution and were loaded with APF (aminophenyl fluorescein, 10 μM) by incubation for 30 min at 37° C. After the second wash, fluorescence images were acquired using a confocal laser scanning microscope LSM 510 (Carl Zeiss Co, Ltd.). The excitation and emission wavelengths were 490 and 515 nm. Alternatively, fluorescence intensity of hyperoxia-exposed cells plated in 24-well plates loaded with APF (10 μM) in the presence and absence of uric acid was assayed using SpectraMax spectrophotometer (Molecular Devices, Sunnyvale, Calif.). Protein tyrosine nitration was measured by Western blot using antinitrotyrosine antibody.

Measurement of Superoxide Radicals

After hyperoxic exposure, cells were loaded with 10 μM dihydroethidine (DHE) for 30 min. After washing, fluorescence images were acquired using a confocal laser scanning microscope LSM 510. The excitation and emission wavelengths were 510 nm and 590 nm. Alternatively, fluorescence intensity of hyperoxia-exposed cells plated in 24-well plates loaded with DHE (10 μM) in the presence and absence of tiron was assayed using SpectraMax spectrophotometer.

Immunofluorescence Confocal Microscopy

Confluent control PAEC or PAEC exposed to hyperoxia (95% $O_2$ and 5% $CO_2$, 24 h) were fixed in 4% paraformaldehyde and then incubated with 0.1% Triton X-100 for 10 min and with 5% goat serum for 30 min. eNOS and F-actin were then stained with mouse anti-eNOS antibody labeled with FITC-goat anti-mouse IgG and Texas red-phalloidin. After the unbound molecules were washed off, eNOS and actin immunofluorescence were assessed using a Zeiss LSM 510 laser scanning confocal microscope.

Statistical Analysis

In each experiment, experimental and control cells were matched for cell line, age, seeding density, number of passages, and number of days postconfluence to avoid variation in tissue culture factors that can influence measurements of peroxynitrite, NO, and superoxide production. One-way ANOVA and post t test analyses were used to determine the significance of differences between the means of different groups. $p<0.05$ was considered statistically significant.

Results

Figure 8A:
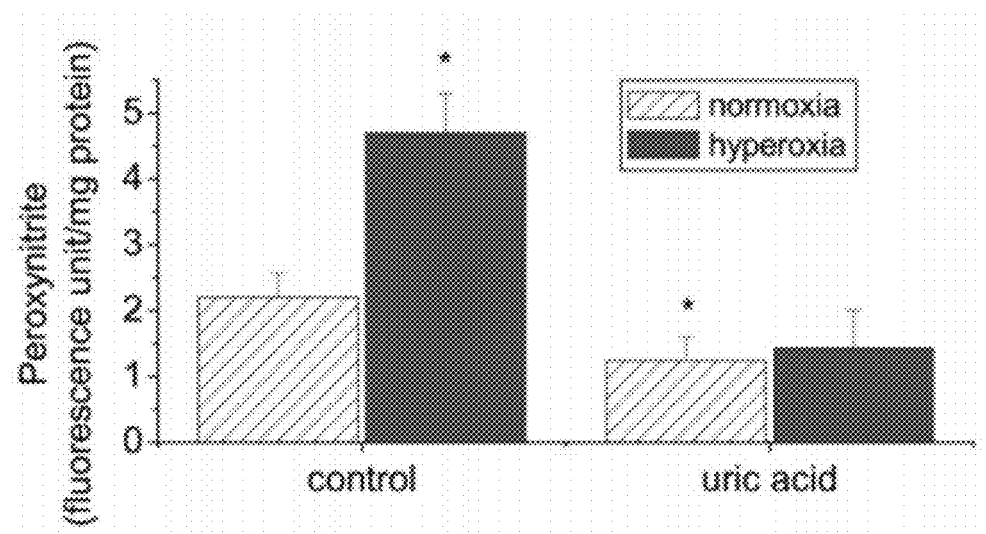
FIGS. 8A and 8B are bar graphs showing the formation of peroxynitrite (FIG. 8A) and superoxide radicals (FIG. 8B) in lung endothelial cells (PAECs) exposed to 95% oxygen for 24 h in the presence or absence of uric acid (FIG. 8A, 100 µM) or tiron (FIG. 8B, 5 mM) and then loaded with APF (FIG. 8A, 10 µM) for 30 min or DHE (FIG. 8B, 10 µM) for 15 min. Results are expressed as mean±S.D.; n=3 experiments. *, p<0.05 versus normoxia control.

To study the effect of hyperoxia on the formation of peroxynitrite, PAEC were exposed to 95% oxygen in the presence and absence of uric acid, a peroxynitrite scavenger, for 24 h. Peroxynitrite level in the cells was measured by using a peroxynitrite-specific fluorescence probe APF which does not react with NO, superoxide, and hydrogen peroxide (Saito, S., et al. (2006) *Plant Cell Physiol.* 47, 689-697). Fluorescence level in cells exposed to hyperoxia was much higher than those exposed to normoxia (FIG. 8A). The presence of uric acid prevented hyperoxia-induced increase in the fluorescence intensity (FIG. 8A), indicating that the fluorescence of APF is due to the increase in peroxynitrite formation. Thus, these results indicate that hyperoxia induces the formation of peroxynitrite in lung endothelial cells.

Figure 8B:
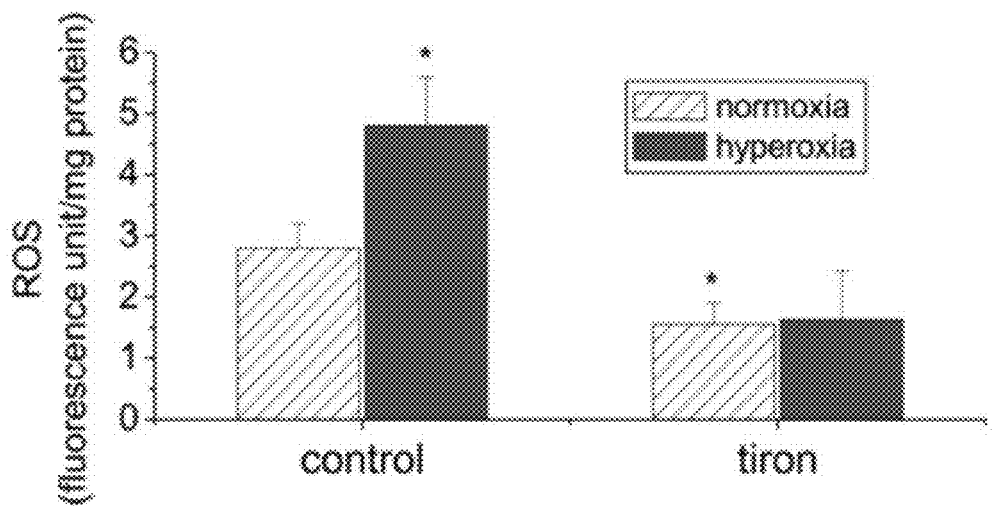

To investigate whether hyperoxia increases ROS formation, the level of $O_2^-$, was determined using the fluorescent dye dihydroethidium (DHE) as previously reported (Carter, WO., et al. (1994) *J. Leukoc. Biol.* 55, 253-258). In the presence of $O_2^-$, DHE is converted to the fluorescent molecule hydroethidium and ethidium. Both products intercalate with DNA that can be detected by fluorescence confocal microscopy and fluorescence spectroscopy. As shown in FIG. 8B, exposure of PAEC to hyperoxia for 24 h led to an increase in the fluorescence intensity. Superoxide radical scavenger tiron prevented the increase in the fluorescence intensity in hyperoxic PAEC (FIG. 8B). These data indicate that exposure to hyperoxia increases superoxide radical level in lung endothelial cells.

Example 10

Exposure of PAEC to Hyperoxia Increases eNOS Activity

Materials and Methods

Determination of eNOS Catalytic Activity and NO Production

After exposure to normoxic or hyperoxic environments, the PAEC monolayers were scraped and homogenized in buffer A (50 mM Tris•HCl, pH 7.4, containing 0.1 mM each EDTA and EGTA, 1 mM phenylmethylsulfonyl fluoride, 1.0 μg/ml leupeptin, and 10 μM calpain inhibitor I). The homogenates were centrifuged at 100,000 g for 60 min at 4° C., and the total membrane pellet was resuspended in buffer B (bufferAplus 2.5 mM $CaCl_2$). The resulting suspension was used for determination of eNOS activity by monitoring the formation of L-[$^3$H]citrulline from L-[$^3$H]arginine (Su, Y., et al. (2003) *Am. J. Physiol. Cell Physiol.* 284, C1542-C1549). To determine NO production, thapsigargin (100 nM) was added to the medium of endothelial cells following normoxic or hyperoxic exposure. After 60 min of incubation, culture medium was collected and ethanol-precipitated to remove proteins. 50 μl of the reaction mix were loaded to the SIEVERS machine for $NO_x$ ($NO_2$ and $NO_3$) measurement according to standard manufacturer's instruction as previously described (Church, J E., et al. (2006) *J. Biol. Chem.* 281, 1477-1488). Protein contents in the cell lysates were determined by Lowry's method.

Results

Figure 9:
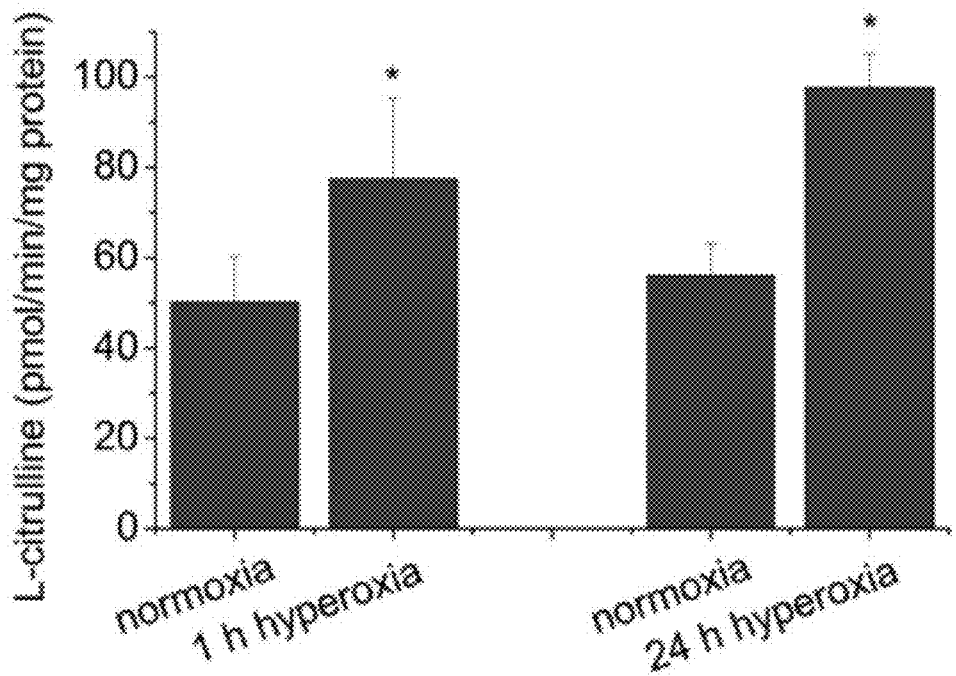
FIG. 9 is a bar graph showing eNOS activity (L-citrulline production (pmol/min/mg protein) in lung endothelial cells (PAECs) exposed to 95% oxygen for 1-24 h. Results are expressed as mean±S.D.; n=3 experiments. *, p<0.05 versus normoxia.

To study the role of eNOS in the hyperoxia-induced increase in peroxynitrite formation in lung endothelial cells, eNOS activity was measured in normoxic and hyperoxic PAEC. As shown in FIG. 9, exposure of PAEC to 95% of oxygen for 1 to 24 h caused an increase in eNOS activity. However, the eNOS protein contents in hyperoxic PAEC remained unchanged (FIG. 9), indicating that hyperoxia increases eNOS activity through a posttranslational mechanism.

Example 11

Effect of Hyperoxia on eNOS-β-Actin Association in PAEC

Materials and Methods

Co-immunoprecipitation of eNOS and β-Actin

The PAEC lysates were incubated with anti-eNOS antibody, non-immune IgG at 4° C. overnight. 30 μl of protein A-Sepharose was added, and samples were further incubated for 2 h at 4° C. Immunoprecipitates were collected by centrifugation and washed three times in buffer containing 50 mM Tris•HCl, pH 7.5, 150 mM NaCl, and 0.1% Triton X-100. Proteins were eluted from Sepharose beads by boiling the samples in 30 μl of SDS immunoblotting sample buffer. Sepharose beads were pelleted by centrifugation at 10,000 μg, and supernatants were analyzed for eNOS and β-actin by Western blotting.

Results eNOS is associated with β-actin in endothelial cells and that association of eNOS with β-actin increases eNOS activity and NO production (Kondrikov, D., et al. (2006) Am. J. Physiol. Lung Cell Mol. Physiol. 290, L41-L50; Su, Y., et al.

Figure 10:
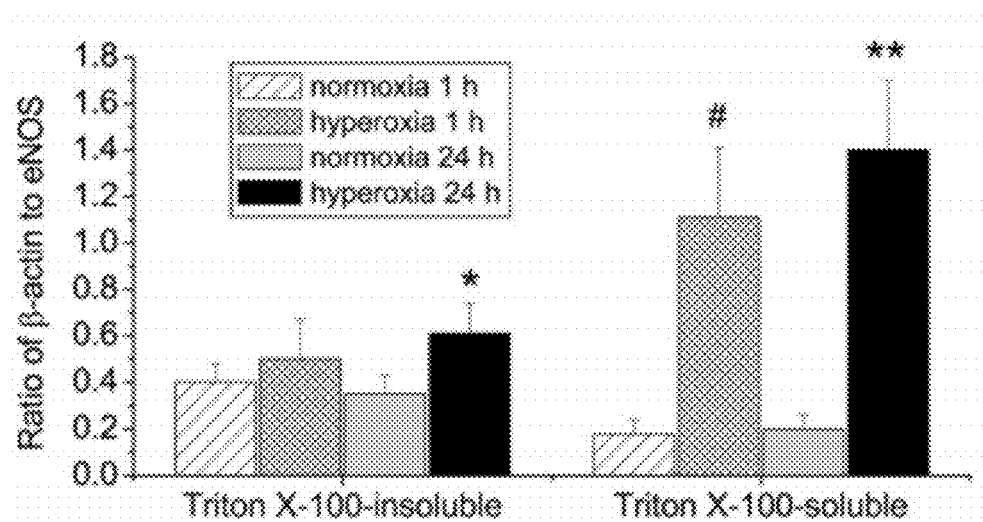
FIG. 10 is a bar graph showing the ratio of β-actin to eNOS in Triton X-100-insoluble (left set of bars) and soluble (right set of bars) fractions of cell lysates from PAECs exposed to normoxia (first and third bars in each set) or hyperoxia (95%, second and fourth bars in each set) for 1 h (first two bars in each set) or 24 h (third and fourth bar in each set). Results are expressed as mean±S.D.; n=3 experiments. *, p<0.05 versus normoxia.

(2003) Am. J. Physiol. Cell Physiol. 284, C1542-C1549; Su, Y., et al. (2007) Sci. STKE., e52-1-e52-3). To study the role of eNOS-β-actin interaction in hyperoxia-induced increase in the formation of peroxynitrite, eNOS-β-actin association was evaluated in hyperoxic and normoxic PAEC using co-immunoprecipitation and confocal microscopy. As shown in FIG. 10, exposure of PAEC with hyperoxia for 1 h significantly increased the amount of β-actin co-immunoprecipitated with eNOS in the Triton X-100 soluble fraction which contains mainly G-actin. The increased association of eNOS and G-actin lasted for 24 h. Meanwhile, hyperoxia for 24 h increased the amount of β-actin co-immunoprecipitated with eNOS in the Triton X-100 insoluble fraction which contains mainly F-actin (FIG. 10). Consistent with this result, confocal microscopy revealed that there was an increased co-localization of eNOS and cortical F-actin at plasma membrane in hyperoxic PAEC. These data indicate that hyperoxia increases eNOS association with both G-actin and F-actin in lung endothelial cells.

Example 12

Reducing β-Actin Availability Prevents Hyperoxia-induced Increases in eNOS-β-Actin Association, eNOS Activity, and the Formation of NO and Peroxynitrite Materials and Methods
Transfection of β-Actin siRNA
To reduce β-actin availability to eNOS, the β-actin mRNA was silenced using its siRNA as previously reported by us (Kondrikov, D., et al. (2006) Am. J. Physiol. Lung Cell Mol. Physiol. 290, L41-L50). Pre-confuorescent PAEC were transfected with 1 μg of β-actin siRNA or a scramble control siRNA (Silencer β-actin siRNA kit, Ambion) using Qiagen RNAiFest transfection reagent in RPMI containing 4% FBS according to the manufacturer's protocol. The ratio of siRNA to transfection reagent was 1:3. Three days after transfection, PAEC were exposed to hyperoxia or normoxia before being used for co-immunoprecipitation and assays of eNOS activity and NO and peroxynitrite formation. Cell number, protein content, and LDH release were comparable between cells transfected with β-actin siRNA and scramble control siRNA indicating that the injury of β-actin knock-down to PAEC is minimal (Kondrikov, D., et al. (2006) Am. J. Physiol. Lung Cell Mol. Physiol. 290, L41-L50).

Figure 11A:
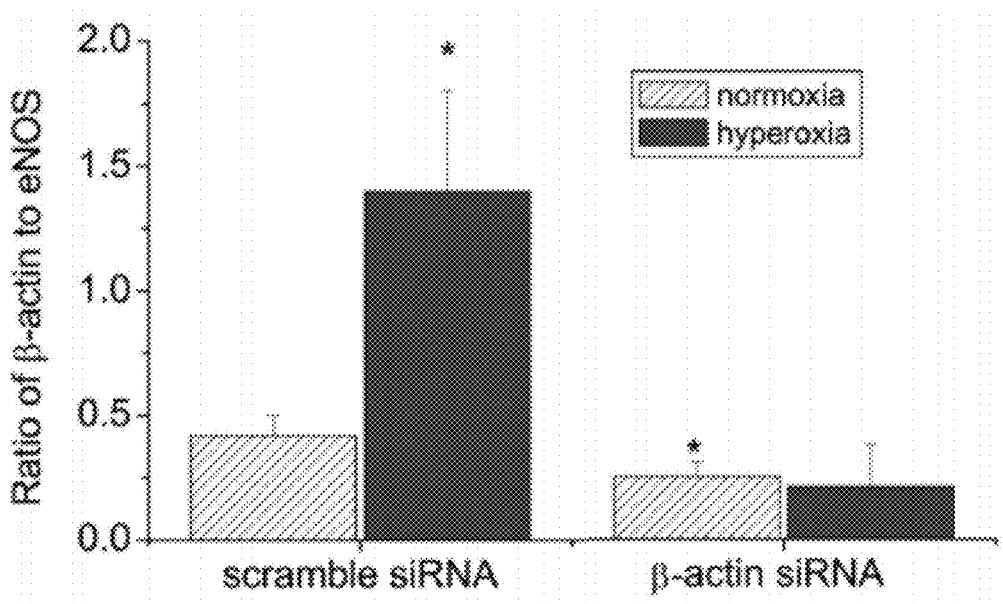
FIGS. 11A-11D are bar graphs showing that reducing β-actin availability prevents hyperoxia-induced increases in eNOS-β-actin association (FIG. 11A), eNOS activity (FIG. 11B), formation of NO (FIG. 11C), and formation of peroxynitrite (FIG. 11D). PAEC were transfected with a scramble siRNA or a siRNA against β-actin. After 48 h, the cells were exposed to normoxia or hyperoxia (95% oxygen) for 24 h. Then, actin association (FIG. 11A), eNOS activity (FIG. 11B), NO (FIG. 11C), and peroxynitrite (FIG. 11D) were determined. Results are expressed as mean±S.D.; n=3 experiments. *, p<0.05 versus normoxia in scramble siRNA group. **, p<0.05 versus normoxia group; #, p<0.05 versus control (without uric acid).
Figure 11B:
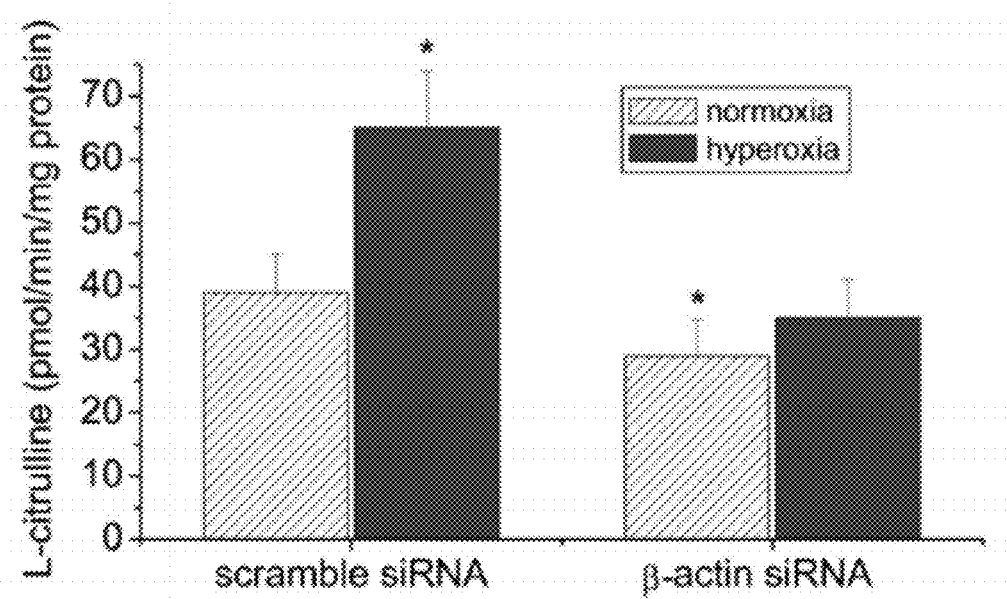
Figure 11C:
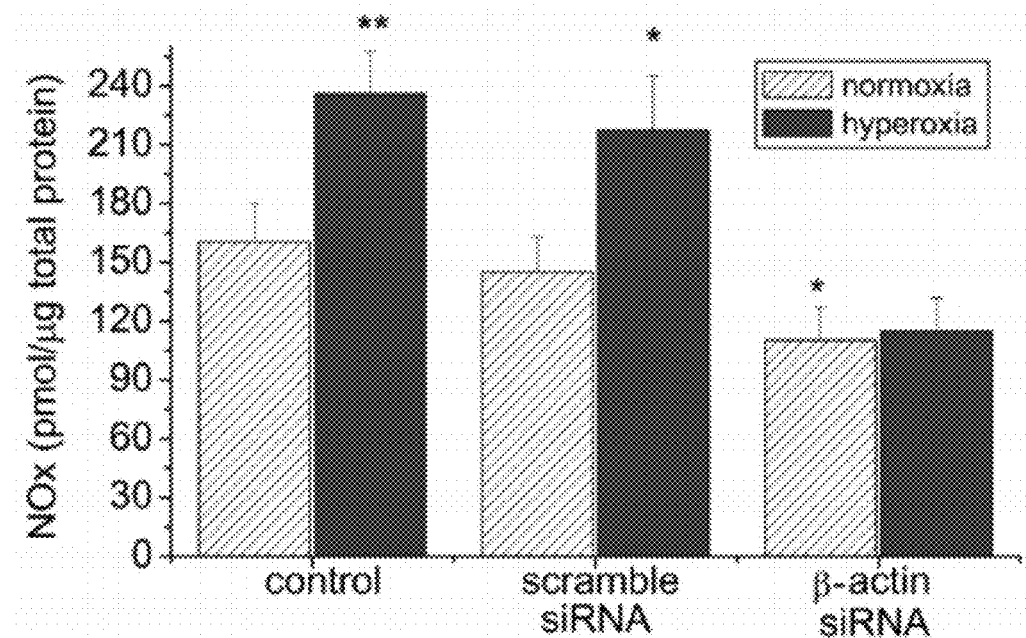
Figure 11D:
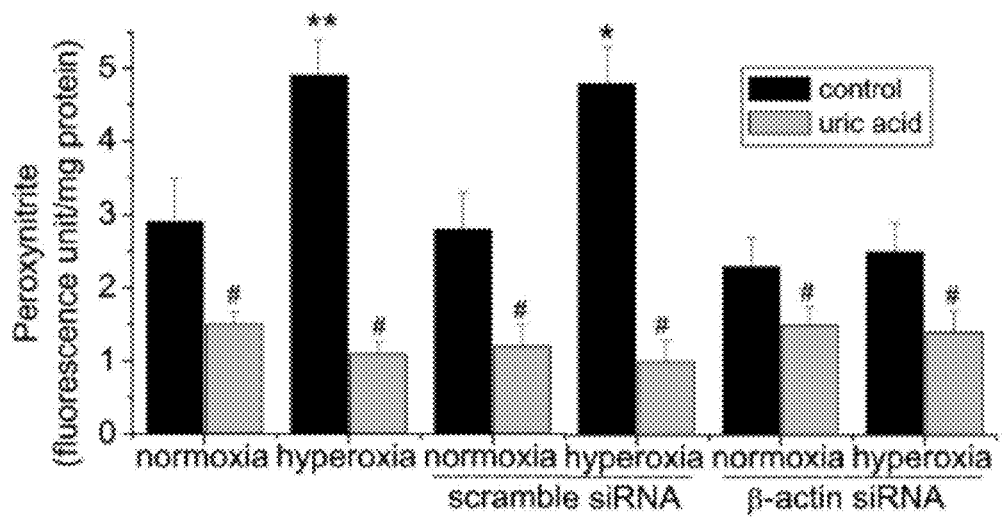

Results
To further analyze the role of eNOS-β-actin interaction in hyperoxia-induced increase in the formation of NO and peroxynitrite, eNOS-β-actin association was disrupted by reducing β-actin availability in PAEC using siRNA technology (Kondrikov, D., et al. (2006) Am. J. Physiol. Lung Cell Mol. Physiol. 290, L41-L50). Transfection of PAEC with β-actin siRNA resulted in a decrease in β-actin protein level by nearly 70% at both normoxic and hypoxic conditions. Silencing β-actin did not cause cellular injury to PAEC (Kondrikov, D., et al. (2006) Am. J. Physiol. Lung Cell Mol. Physiol. 290, L41-L50). Interestingly, hyperoxia failed to induce an increase in the amount of β-actin co-immunoprecipitated with eNOS in PAEC transfected with β-actin siRNA (FIG. 11A). In addition, reducing β-actin availability prevented hyperoxia-induced increase in eNOS activity (FIG. 11B). These data indicate that inhibition of eNOS-β-actin association prevents hyperoxia-induced increase in eNOS activity. NO and peroxynitrite production were then measured in endothelial cells in which eNOS-β-actin association was disrupted by β-actin siRNA. In the presence of scramble siRNA, exposure of PAEC to hyperoxia induced a remarkable increase in NO and peroxynitrite formation (FIGS. 11C and 11D). Transfection of endothelial cells with β-actin siRNA significantly inhibited hyperoxia-induced increases in the formation of NO and peroxynitrite (FIGS. 11C and 11D).

Example 13

Synthetic Peptide P326TAT Prevents eNOS-β-Actin Association, Peroxynitrite Formation, and Protein Tyrosine Nitration in Hyperoxia-exposed PAEC Materials and Methods
Inhibition of eNOS-β-Actin Interaction using Peptide
The actin binding site on eNOS protein has been identified as being at amino acid residues 326-333 and hydrophobic residues leucine 326, leucine 328, tryptophan 330, and leucine 333 in the actin binding site are essential for actin binding (Kondrikov, D., et al. (2010) J. Biol. Chem. 285, 4319-4327). To study the role of eNOS-β-actin interaction on eNOS activity, NO release, and peroxynitrite formation, peptide (P326TAT) with amino acid sequence corresponding to the actin binding region of eNOS residues 326-333 linked to an 10 amino acid transduction domain of HIVTAT (RKKRRQRRRA, SEQ ID NO:43) was synthesized by GeneScript Corporation (Piscataway, N.J.). A modified version of ABS peptide 326 with hydrophobic leucine and tryptophan substituted for neutrally charged alanine was used as a control peptide. The amino acid sequences of the peptides are RKKRRQRRRALGLRWYAL (SEQ ID NO:2) for P326TAT and RKKRRQRRRAAGARAYAA (SEQ ID NO:14) for control peptide (PlwTAT). PAEC were incubated with P326TAT or PlwTAT at 20 μM final concentration in MEM medium. After 1 h initial transfection, RPMI medium containing 4% FBS was added to reach final concentration of 2% FBS. Cells were then exposed to hyperoxia or normoxia before being used for co-immunoprecipitation and assays of eNOS activity, NO and peroxynitrite formation, and protein tyrosine nitration.

Results
The P326TAT peptide specifically binds to β-actin and competitively inhibits eNOS-β-actin association in vitro and in intact endothelial cells (Kondrikov, D., et al. (2010) J. Biol. Chem. 285, 4319-4327). To study whether peptide P326TAT prevents hyperoxia-induced increase in eNOS-β-actin association, endothelial cells were transfected with peptide 326 linked to an 11-amino acid transduction domain of HIV TAT (P326TAT) as described by Gustafsson et al. (Carter, WO., et al. (1994) J. Leukoc. Biol. 55, 253-258). This TAT tag can be used to facilitate delivery of biologically active proteins or peptides into cells and tissues through the fusion of a protein transduction domain to the protein or peptide of interest (Li, J., et al. (2004) Free Radic. Biol. Med. 36, 1460-1470).

Figure 12A:
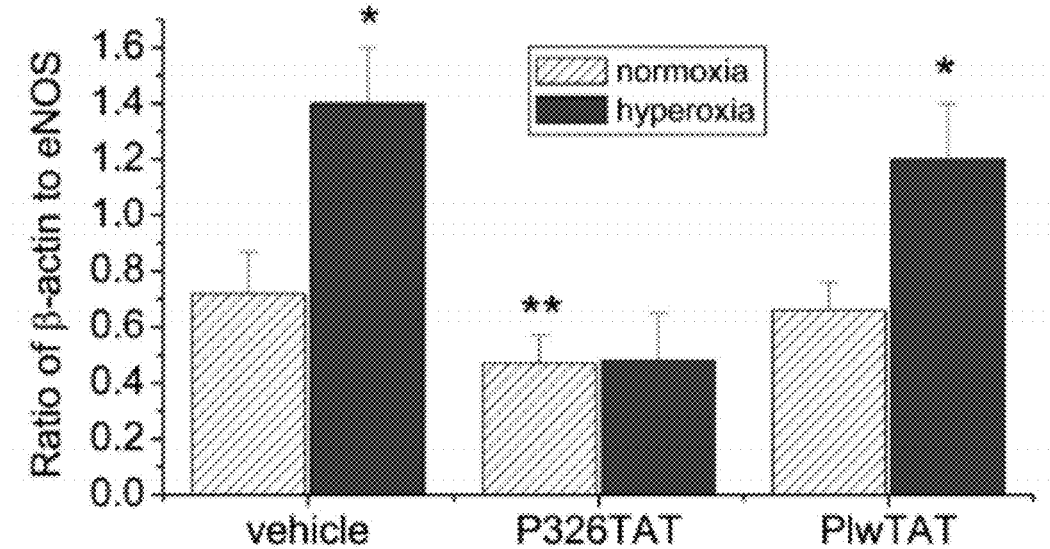
Figure 12B:
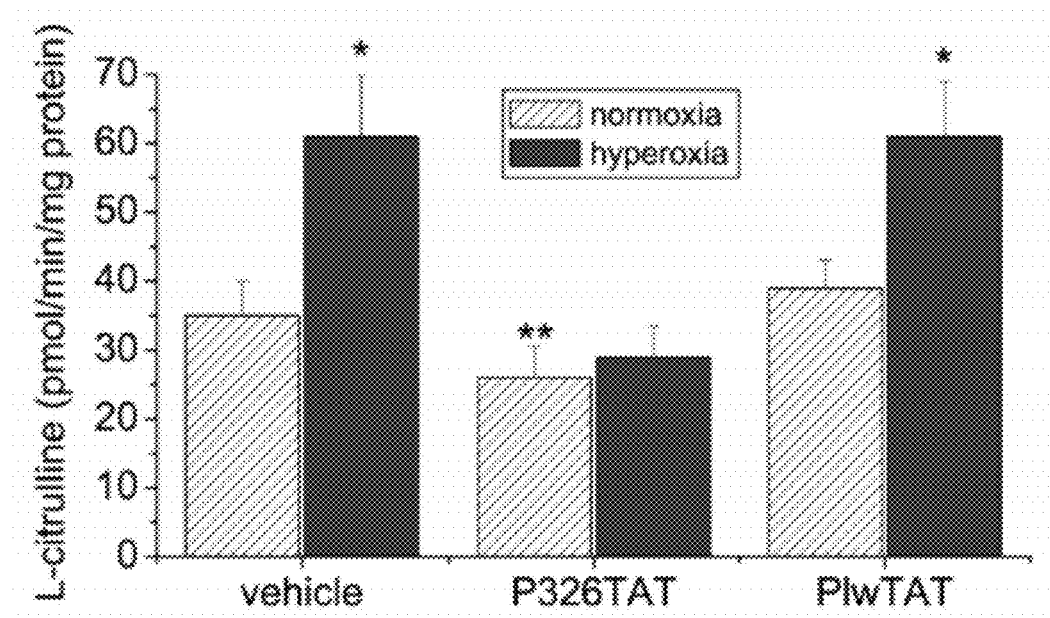

P326TAT and control peptide PlwTAT can enter endothelial cells efficiently (Kondrikov, D., et al. (2010) J. Biol. Chem. 285, 4319-4327). As shown in FIG. 12A, incubation of endothelial cells with peptide P326TAT significantly decreased the amount of β-actin co-immunoprecipitated with eNOS and prevented hyperoxia-induced increase in eNOS-β-actin co-immunoprecipitation. eNOS activity, NO and peroxynitrite production were then measured in P326TAT-transfected endothelial cells exposed to normoxic and hyperoxic conditions. As shown in FIG. 12B, hyperoxic exposure did not induce an increase in eNOS activity in P326TAT transfected cells, compared to cells transfected with control peptide PlwTAT. Moreover, P326TAT prevented hyperoxiainduced increases in NO and peroxynitrite formation (FIGS.

Figure 13:
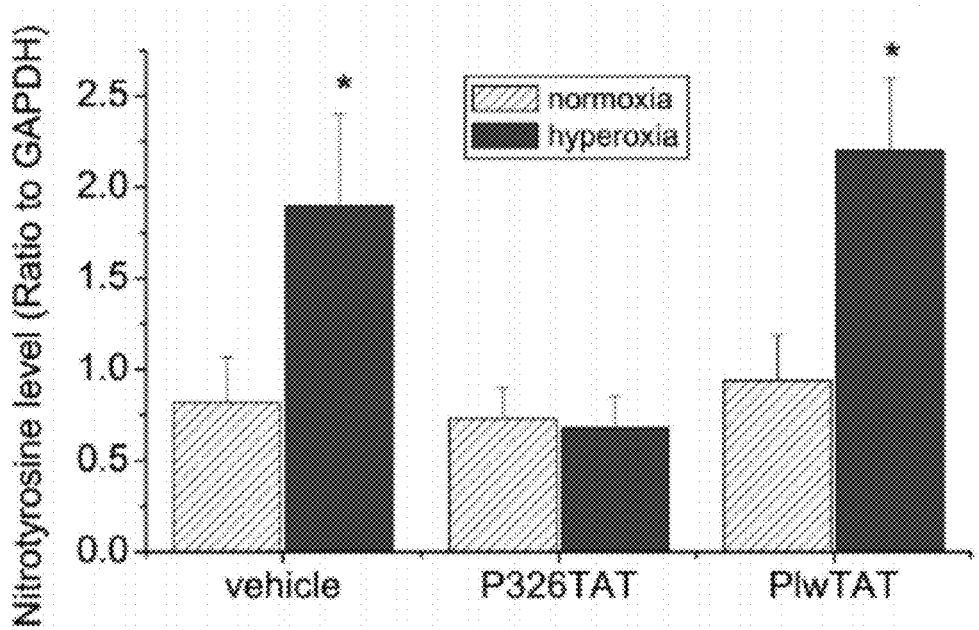
FIG. 13 is a bar graph showing the effect of the synthetic peptides P326TAT and PlwTAT on hyperoxia-induced increase in protein tyrosine nitration of proteins at 250, 100, 75, and 60 kDa. PAEC were exposed to normoxia or hyperoxia (95% oxygen) in the presence and absence of P326TAT or PlwTAT at final concentration 20 µM for 24 h. Results are expressed as mean±S.D.; n=3 experiments. *, p<0.05 versus normoxia group.

12C and 12D). Furthermore, to study whether alterations in peroxynitrite formation lead to changes in protein tyrosine nitration, protein nitrotyrosine in PAEC treated with or without PlwTAT and P326TAT under normoxic and hyperoxic conditions was assayed. As shown in FIG. 13, hyperoxia induced the increases in tyrosine nitration of proteins at 250, 100, 75, and 60 kDa in PAEC treated with or without control peptide PlwTAT. The levels of tyrosine nitration proteins at 250, 100, 75, and 60 kDa in PAEC treated with P326TAT were comparable between normoxia and hyperoxia (FIG. 13). These results show that peptide P326TAT prevents hyperoxia-induced increases in eNOS-β-actin association, eNOS activity, the formation of NO and peroxynitrite, and protein tyrosine nitration in PAEC.

Example 14

Mutation of β-Actin Binding Domain in eNOS Protein Prevents Hyperoxia-induced eNOS-β-Actin Association and Peroxynitrite Formation Materials and Methods
Site-directed Mutagenesis of eNOS and Transfection of COS-7 Cells with Wild Type and eNOS Mutant Hydrophobic residues leucine 326, leucine 328, tryptophan 330, and leucine 333 in the actin binding site are critical for eNOS-β-actin interaction. To study the role of eNOS-β-actin interaction on eNOS activity, NO release, and peroxynitrite formation, residues leucine 326, leucine 328, tryptophan 330, and leucine 333 in the actin binding site were replaced with alanine by using site-directed mutagenesis (Kondrikov, D., et al. (2010) *J. Biol. Chem.* 285, 4319-4327). Plasmids containing wild type eNOS cDNA or eNOS mutant cDNA were transfected into COS-7 cells using Lipofectamine LTX with PLUS reagent (Invitrogen, Carlsbad, Calif.) according to the manufacturer's protocol. 48 h after transfection, cells were exposed to hyperoxia or normoxia and then subjected to eNOS-β-actin co-immunoprecipitation and assays for eNOS activity, NO generation, and peroxynitrite formation.

Figure 14A:
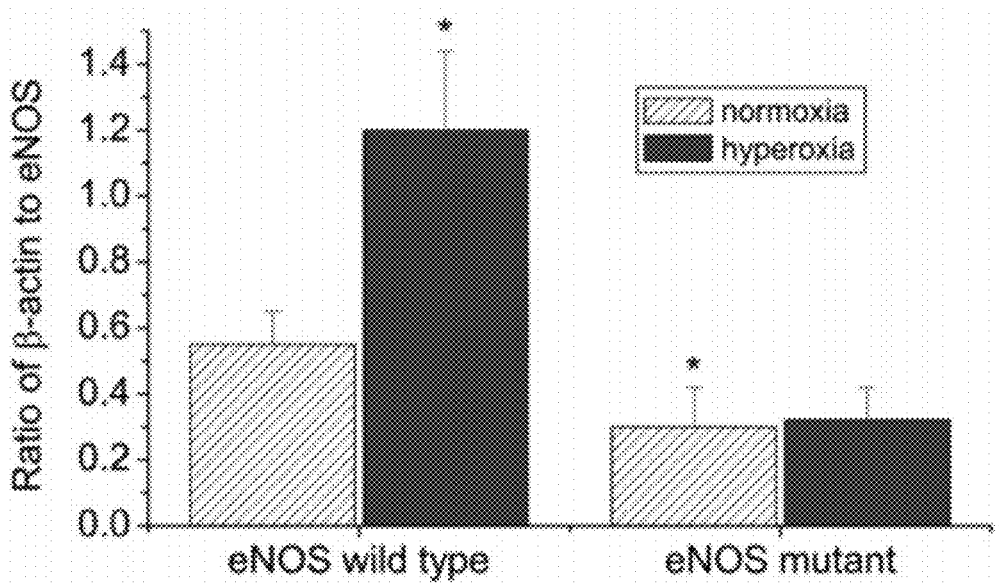
FIG. 14A-14D are bar graphs showing the effect of mutating the β-actin binding domain in eNOS protein on eNOS-β-actin association (FIG. 14A), hyperoxia-induced increase in eNOS activity (FIG. 14B), formation of NO (FIG. 14C), and formation of peroxynitrite (FIG. 14D) in COS-7 cells. COS-7 cells transfected with wild type and mutant eNOS plasmids were exposed to normoxia or hyperoxia (95% oxygen) for 24 h. Results are expressed as mean±S.D.; n=3 experiments. *, p<0.05 versus normoxia in wild-type group; #, p<0.05 versus control (without uric acid).
Figure 14B:
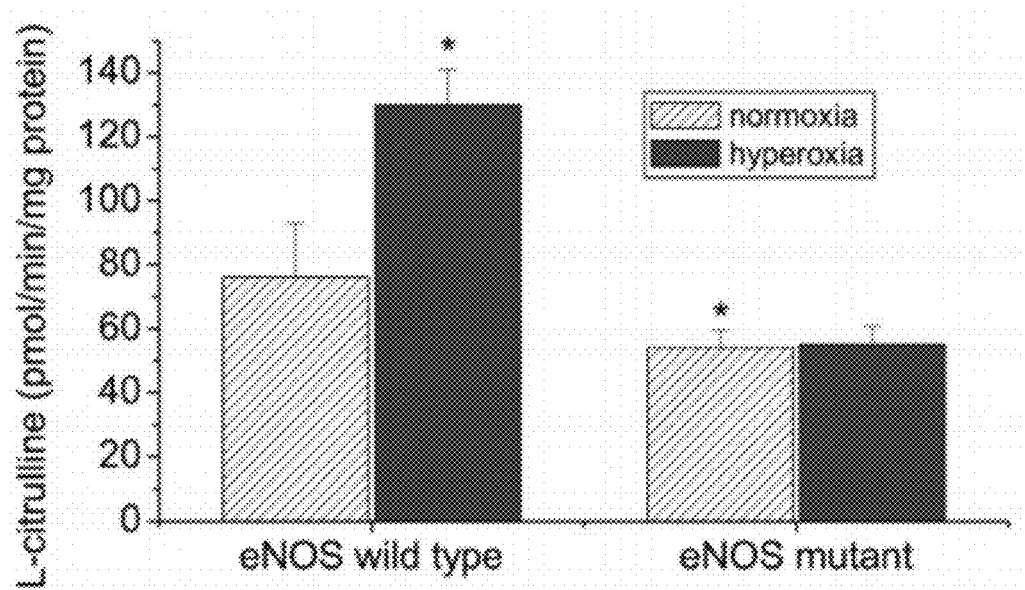
Figure 14C:
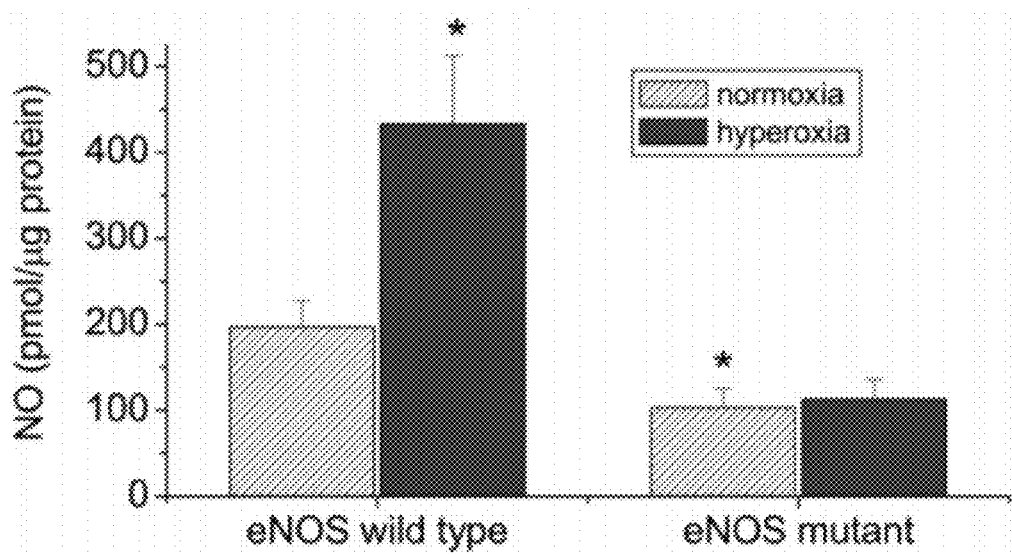
Figure 14D:
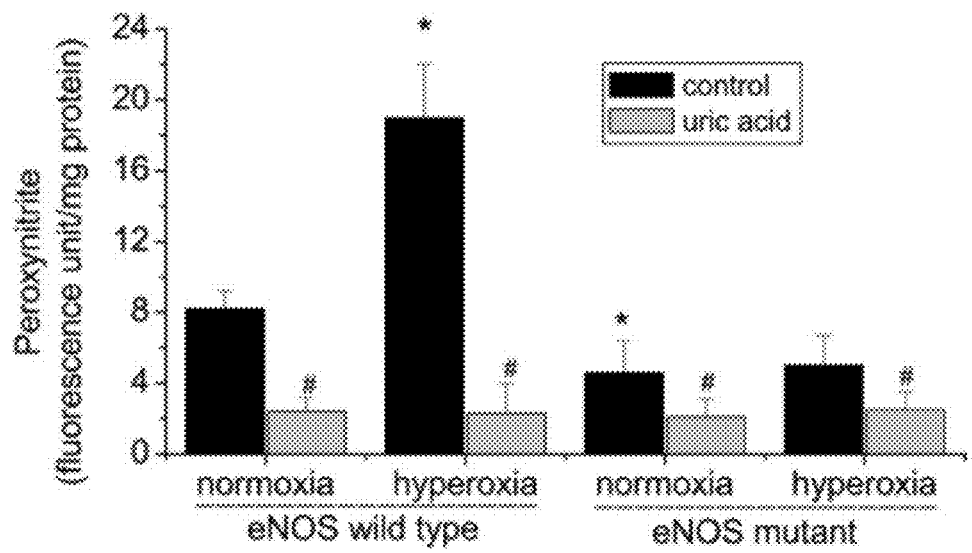

Results
The hydrophobic amino acids residues leucine 326, leucine 328, tryptophan 330, and leucine 333 within β-actin binding domain of eNOS are critical for eNOSβ-actin interaction (Kondrikov, D., et al. (2010) *J. Biol. Chem.* 285, 4319-4327). To further study the role of eNOS-β-actin interaction in hyperoxia-induced increase in peroxynitrite formation, residues leucine 326, leucine 328, tryptophan 330, and leucine 333 in the β-actin binding domain of eNOS were replaced for alanine by site-directed mutagenesis. The plasmids containing wild type and mutant eNOS genes were transfected into COS-7 cells. As shown in FIG. 14A, hyperoxia increased the amount of β-actin co-precipitated with eNOS in COS-7 cells transfected with the plasmids containing wild-type eNOS gene but failed to increase the amount of β-actin co-precipitated with eNOS mutant in COS-7 cells transfected with the plasmids containing eNOS mutant gene. More importantly, the increases in eNOS activity and the formation of NO and peroxynitrite induced by hyperoxia were prevented in COS-7 cells containing eNOS mutant gene (FIGS. 14B and 14C). The inhibition of hyperoxia-induced increase in NO and peroxynitrite generation in COS-7 cells containing eNOS mutant gene are not due to the direct effect of the mutation on eNOS activity, because the catalytic activity from purified wild type and mutated eNOS were comparable (Kondrikov, D., et al. (2010) *J. Biol. Chem.* 285, 4319-4327). Taken together, these results indicate that disruption of eNOS-β-actin association prevents hyperoxia-induced increases in eNOS activity and the formation of NO and peroxynitrite.

Example 15

Hyperoxia Induces Increases in eNOS-β-Actin Association, eNOS Activity, and Protein Tyrosine Nitration in Mouse Lungs Materials and Methods
Exposure of Mice to Hyperoxia
Male C57BL/6 mice were purchased from the Jackson Laboratory (Bar Harbor, Me.). Animals with ages between 8 and 10 weeks were used. All experiments were performed in accordance with the guiding principles of the Guide for the Care and Use of Laboratory Animals and approved by the Institutional Animal Care and Use Committee (IACUC) of the Medical College of Georgia. Mice were exposed to hyperoxia in a clear plastic polypropylene chamber (30'×20'×20') for 5 days ad libitum with free access to food and water. The oxygen concentration (85% oxygen) was maintained using Proox Oxygen Controller (BioSpherix, Lacona, N.Y.). The oxygen mixture was humidified, and the concentration of $CO_2$ in the chamber was lower than 0.3%. Control mice were kept in room air.

Mouse Lung Experiments
Mice were anesthetized (pentobarbital, 90 mg/kg, intraperitoneal), and the trachea was intubated. The mice were then euthanized by using thoracotomy. The blood in pulmonary circulation was rinsed by infusing PBS through pulmonary artery. Then the lungs were removed and snap-frozen in liquid nitrogen for preparing homogenates. The assays of eNOS catalytic activity, protein tyrosine nitration, and co-immunoprecipitation of eNOS and β-actin were performed using the lung homogenates.

Figure 15A:
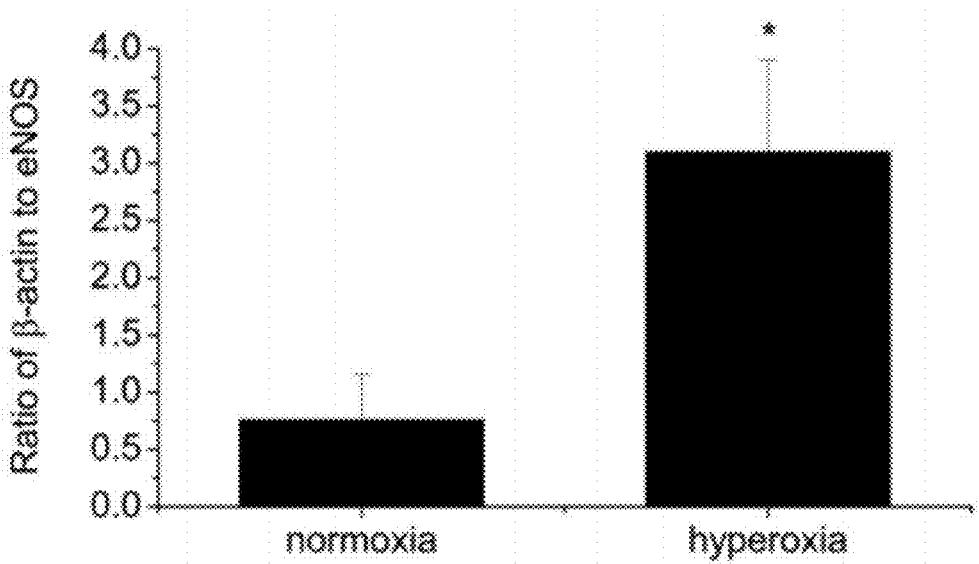
FIGS. 15A-15C are bar graphs showing the effect of hyperoxia on eNOS-β-actin association (FIG. 15A), hyperoxia-induced increase in eNOS activity (FIG. 15B), formation of NO (FIG. 14C), and protein tyrosine nitration (FIG. 15D) in lung homogenates of male C57BL/6 mice exposed to 85% oxygen for 5 days. Results are expressed as mean±S.D.; n=10 experiments. *, p<0.05 versus normoxia control.
Figure 15B:
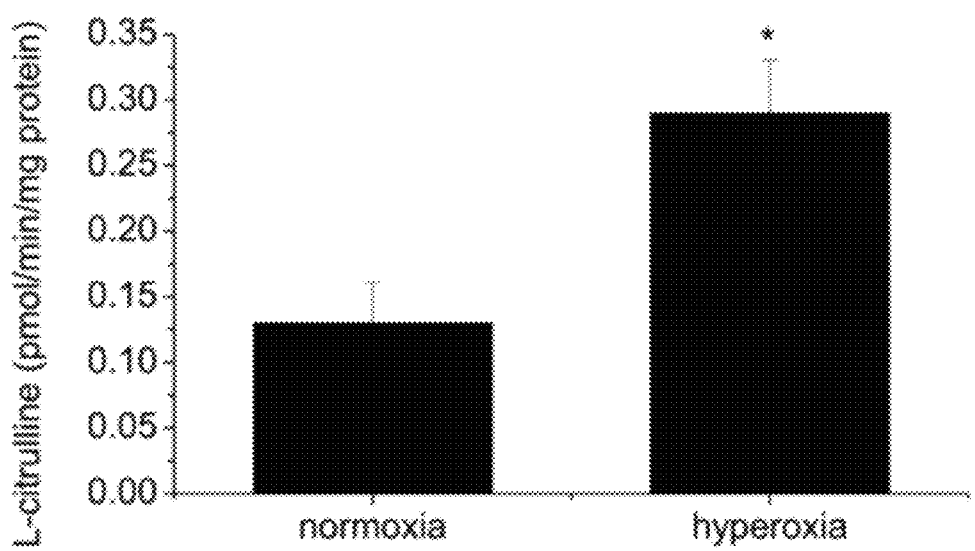
Figure 15C:
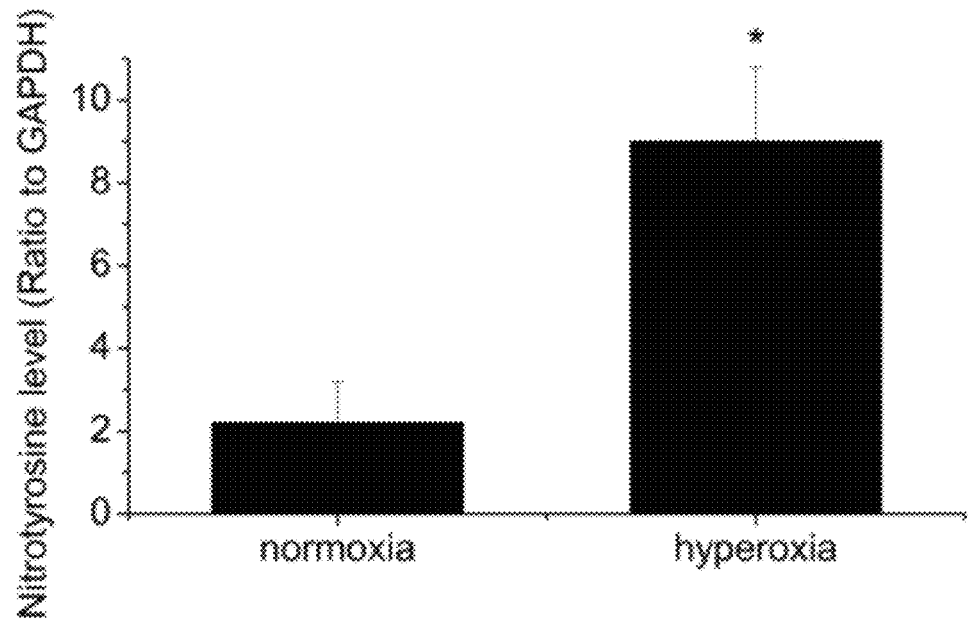

Results
To study whether hyperoxia causes alterations in eNOS-β-actin association, eNOS activity, and protein tyrosine nitration in mouse lungs, male C57BL/6 mice were exposed to 85% oxygen for 5 days, then eNOS-β-actin association, eNOS activity, and protein nitrotyrosine were assayed in the lung homogenates. As shown in FIG. 15A, the eNOS protein contents were comparable between normoxic and hyperoxic lungs. However, the amount of β-actin co-immunoprecipitated with eNOS was much larger in the homogenates from hyperoxic lungs than those from normoxic lungs, suggesting that hyperoxia induces an increase in eNOS-β-actin association in mouse lungs. Correspondingly, eNOS activities were much higher in hyperoxic lungs than in normoxic lungs (FIG. 15B). Furthermore, nitrotyrosine protein contents were much higher in hyperoxic lungs than those in normoxic lungs (FIG. 15C). These data indicate that hyperoxia induces increases in eNOS-β-actin association, eNOS activity, and protein tyrosine nitration in mouse lungs.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated polypeptide 6 to 30 residues in length comprising an amino acid sequence that is at least 75% identical to SEQ ID NO:1 (LGLRWYAL), wherein the polypeptide is operably linked to a cell penetrating peptide, wherein the polypeptide binds β-actin.

2. The isolated polypeptide of claim 1, wherein the polypeptide binds to β-actin in vivo.

3. The isolated polypeptide of claim 1, wherein the polypeptide comprises a conservative amino acid substitution in SEQ ID NO:1.

4. The isolated polypeptide of claim 3, wherein the polypeptide comprises at least 6 consecutive amino acids of SEQ ID NO:1.

5. The isolated polypeptide of claim 1, wherein the cell penetrating peptide is TAT.

6. The isolated polypeptide of claim 5, wherein the polypeptide comprises the amino acid sequence SEQ ID NO:2 (RKKRRQRRRALGLRWYAL).

7. The isolated polypeptide of claim 1 operably linked to a lung-homing peptide.

8. The isolated polypeptide of claim 7, wherein the lung-homing peptide is the tripeptide motif gly-phe-glu (GFE).

9. A synthetic or recombinant polypeptide comprising the β-actin binding domain of eNOS, wherein the polypeptide inhibits eNOS activity in lung endothelial cells, and wherein the polypeptide consists of SEQ ID NO:2.

10. A pharmaceutical composition comprising an effective amount of the polypeptide of any one of claims 1-4, and 5-9 to inhibit or reduce eNOS binding to β-actin in vivo and a pharmaceutically acceptable excipient.

11. A method of inhibiting eNOS association with β-actin in a cell, comprising contacting the cell with a polypeptide 6 to 30 amino acids in length comprising the amino acid sequence SEQ ID NO:1.

12. The method of claim 11, wherein the polypeptide comprises a cell penetrating peptide.

13. The method of claim 12, wherein the cell penetrating peptide is TAT.

14. The method of claim 13, wherein the polypeptide comprises the amino acid sequence SEQ ID NO:2.

15. The method of claim 12, wherein the polypeptide comprises a lung-homing peptide.

16. The method of claim 15, wherein the lung-homing peptide is the tripeptide motif gly-phe-glu (GFE).

17. The method of any one of claims 11 to 16, wherein the polypeptide inhibits or reduces damage in the cell from hyperoxia.

18. A method of inhibiting peroxynitrite formation in a cell, comprising contacting the cell with a polypeptide comprising the β-actin binding domain of eNOS, wherein the polypeptide inhibits eNOS activity in the cell.

19. The method of claim 18, wherein the β-actin binding domain of eNOS comprises the amino acid sequence SEQ ID NO:1.

20. The method of claim 18, wherein the polypeptide comprises a cell penetrating peptide.

21. The method of claim 20, wherein the cell penetrating peptide is TAT.

22. The method of claim 21, wherein the polypeptide comprises the amino acid sequence SEQ ID NO:2.

23. The method of claim 20, wherein the polypeptide comprises a lung-homing peptide.

24. The method of claim 23, wherein the lung-homing peptide is the tripeptide motif gly-phe-glu (GFE).

25. A method of inhibiting, reducing or attenuating lung damage by hyperoxia in a subject, comprising administering to the subject a therapeutically effective amount of a polypeptide comprising the β-actin binding domain of eNOS, wherein the purified polypeptide does not comprise full-length eNOS.

26. The method of claim 25, wherein the β-actin binding domain of eNOS comprises the amino acid sequence SEQ ID NO:1 (LGLRWYAL), and wherein the polypeptide further comprises a cell penetrating peptide.

27. The method of claim 26, wherein the cell penetrating peptide is TAT.

28. The method of claim 27, wherein the polypeptide comprises the amino acid sequence SEQ ID NO:2.

29. The method of claim 27, wherein the polypeptide comprises a lung-homing peptide.

30. The method of claim 29, wherein the lung-homing peptide is the tripeptide motif gly-phe-glu (GFE).

31. An isolated fragment of eNOS consisting of SEQ ID NO:1.

32. An isolated β actin-binding polypeptide consisting of SEQ ID NO:1.

* * * * *

SEQUENCE LISTING

<160> NUMBER OF SEQ ID NOS: 44

<210> SEQ ID NO 1
<211> LENGTH: 8
<212> TYPE: PRT
<213> ORGANISM: Homo sapiens

<400> SEQUENCE: 1

Leu Gly Leu Arg Trp Tyr Ala Leu
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

Arg Lys Lys Arg Arg Gln Arg Arg Ala Leu Gly Leu Arg Trp Tyr
1               5                   10                  15

Ala Leu

<210> SEQ ID NO 3

<400> SEQUENCE: 3

000

<210> SEQ ID NO 4
<211> LENGTH: 29
<212> TYPE: PRT
<213> ORGANISM: Homo sapiens

<400> SEQUENCE: 4

Asn Val Asp Leu Val Asn Ile Gly Ser Thr Asp Ile Val Asp Gly Asn
1               5                   10                  15

His Lys Leu Thr Leu Gly Leu Ile Trp Asn Ile Ile Leu
            20                  25

<210> SEQ ID NO 5
<211> LENGTH: 29
<212> TYPE: PRT
<213> ORGANISM: Homo sapiens

<400> SEQUENCE: 5

Gln Val Lys Leu Val Asn Ile Arg Asp Asp Ile Ala Asp Gly Asn
1               5                   10                  15

Pro Lys Leu Thr Leu Gly Leu Ile Trp Thr Ile Ile Leu
            20                  25

<210> SEQ ID NO 6
<211> LENGTH: 29
<212> TYPE: PRT
<213> ORGANISM: Homo sapiens

<400> SEQUENCE: 6

Arg Val His Leu Glu Asn Met Gly Ser His Asp Ile Val Asp Gly Asn
1               5                   10                  15

His Arg Leu Val Leu Gly Leu Ile Trp Thr Ile Ile Leu
            20                  25

```
<210> SEQ ID NO 7
<211> LENGTH: 8
<212> TYPE: PRT
<213> ORGANISM: Homo sapiens

<400> SEQUENCE: 7

Leu Gly Leu Ile Trp Asn Ile Ile
1               5

<210> SEQ ID NO 8
<211> LENGTH: 8
<212> TYPE: PRT
<213> ORGANISM: Homo sapiens

<400> SEQUENCE: 8

Leu Gly Leu Leu Trp Thr Ile Ile
1               5

<210> SEQ ID NO 9
<211> LENGTH: 8
<212> TYPE: PRT
<213> ORGANISM: Homo sapiens

<400> SEQUENCE: 9

Leu Gly Leu Ile Trp Tyr Ile Ile
1               5

<210> SEQ ID NO 10
<211> LENGTH: 11
<212> TYPE: PRT
<213> ORGANISM: Homo sapiens

<400> SEQUENCE: 10

Arg Lys Lys Thr Phe Lys Glu Val Ala Asn Ala
1               5                   10

<210> SEQ ID NO 11
<211> LENGTH: 11
<212> TYPE: PRT
<213> ORGANISM: Homo sapiens

<400> SEQUENCE: 11

Gln Lys Lys Thr Phe Thr Lys Trp Val Asn Ala
1               5                   10

<210> SEQ ID NO 12
<211> LENGTH: 11
<212> TYPE: PRT
<213> ORGANISM: Homo sapiens

<400> SEQUENCE: 12

Gln Lys Lys Thr Phe Thr Lys Trp Val Asn Lys
1               5                   10

<210> SEQ ID NO 13
<211> LENGTH: 11
<212> TYPE: PRT
<213> ORGANISM: Homo sapiens

<400> SEQUENCE: 13

Gln Lys Lys Thr Phe Thr Lys Trp Val Asn Ser
1               5                   10

<210> SEQ ID NO 14
<211> LENGTH: 18
<212> TYPE: PRT
```

```
<213> ORGANISM: Artificial Sequence
<220> FEATURE:
<223> OTHER INFORMATION: Synthetic Construct

<400> SEQUENCE: 14

Arg Lys Lys Arg Arg Gln Arg Arg Ala Ala Gly Ala Arg Ala Tyr
1               5                   10                  15

Ala Ala

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = Arg, Ile, or Leu
<220> FEATURE:
<221> NAME/KEY: MISC_FEATURE
<222> LOCATION: (6)..(6)
<223> OTHER INFORMATION: Xaa = Tyr, Asn, or Thr
<220> FEATURE:
<221> NAME/KEY: MISC_FEATURE
<222> LOCATION: (7)..(7)
<223> OTHER INFORMATION: Xaa = Ala or Ile
<220> FEATURE:
<221> NAME/KEY: MISC_FEATURE
<222> LOCATION: (8)..(8)
<223> OTHER INFORMATION: Xaa = Leu or Ile

<400> SEQUENCE: 15

Leu Gly Leu Xaa Trp Xaa Xaa Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(8)
<223> OTHER INFORMATION: Xaa = any amino acid

<400> SEQUENCE: 16

Leu Gly Leu Xaa Trp Xaa Xaa Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Arg Lys Lys Arg Arg Gln Arg Arg Arg
1               5

<210> SEQ ID NO 18
<211> LENGTH: 11
<212> TYPE: PRT
<213> ORGANISM: Artificial Sequence
<220> FEATURE:
```

-continued

<223> OTHER INFORMATION: Synthetic Construct

<400> SEQUENCE: 18

Gly Arg Lys Lys Arg Arg Gln Arg Pro Pro Gln
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Construct

<400> SEQUENCE: 19

Gly Arg Arg Arg Arg Arg Arg Arg Arg Arg Pro Pro Gln
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Thr Arg Gln Ala Arg Arg Asn Arg Arg Arg Arg Trp Arg Glu Arg Gln
1               5                   10                  15

Arg

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Arg Arg Arg Arg Arg Arg Arg Trp
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Gly Arg Lys Lys Arg Arg Gln Arg Arg Arg Pro Trp Gln
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Arg Arg Arg Arg Asn Arg Thr Arg Arg Asn Arg Arg Arg Val Arg
1               5                   10                  15

<210> SEQ ID NO 24
<211> LENGTH: 19
<212> TYPE: PRT
<213> ORGANISM: Artificial Sequence
<220> FEATURE:

```
<223> OTHER INFORMATION: Synthetic Construct

<400> SEQUENCE: 24

Lys Met Thr Arg Ala Gln Arg Arg Ala Ala Arg Arg Asn Arg Trp
1               5                   10                  15

Thr Ala Arg

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Thr Arg Arg Gln Arg Thr Arg Arg Ala Arg Arg Asn Arg
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Synthetic Construct

<400> SEQUENCE: 26

Lys Leu Thr Arg Ala Gln Arg Arg Ala Ala Arg Lys Asn Lys Arg
1               5                   10                  15

Asn Thr Arg

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Asn Ala Lys Thr Arg Arg His Glu Arg Arg Arg Lys Leu Ala Ile Glu
1               5                   10                  15

Arg

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Arg Arg Arg Arg Arg Arg Arg Arg Arg
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic Construct

<400> SEQUENCE: 29

Arg Gln Pro Lys Ile Trp Phe Pro Asn Arg Arg Lys Pro Trp Lys Lys
1               5                   10                  15

<210> SEQ ID NO 30
```

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 30

Arg Gln Ile Lys Ile Trp Phe Gln Asn Arg Arg Met Lys Trp Lys Lys
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Construct

<400> SEQUENCE: 31

Arg Gln Ile Ala Ile Trp Phe Gln Asn Arg Arg Met Lys Trp Ala Ala
1               5                   10                  15

<210> SEQ ID NO 32
<211> LENGTH: 21
<212> TYPE: PRT
<213> ORGANISM: Artificial Sequence
<220> FEATURE:
<223> OTHER INFORMATION: Synthetic Construct

<400> SEQUENCE: 32

Thr Arg Ser Ser Arg Ala Gly Leu Gln Phe Pro Val Gly Arg Val His
1               5                   10                  15

Arg Leu Leu Arg Lys
            20

<210> SEQ ID NO 33
<211> LENGTH: 26
<212> TYPE: PRT
<213> ORGANISM: Artificial Sequence
<220> FEATURE:
<223> OTHER INFORMATION: Synthetic Construct

<400> SEQUENCE: 33

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct

<400> SEQUENCE: 34

Lys Leu Ala Leu Lys Leu Ala Leu Lys Ala Leu Lys Ala Ala Leu Lys
1               5                   10                  15

Leu Ala

<210> SEQ ID NO 35
<211> LENGTH: 16
<212> TYPE: PRT
<213> ORGANISM: Artificial Sequence
<220> FEATURE:
<223> OTHER INFORMATION: Synthetic Construct

<400> SEQUENCE: 35
```

```
Ala Ala Val Ala Leu Leu Pro Ala Val Leu Leu Ala Leu Leu Ala Pro
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: Synthetic Construct

<400> SEQUENCE: 36

Leu Leu Ile Ile Leu Arg Arg Arg Ile Arg Lys Gln Ala His Ala His
1               5                   10                  15

Ser Lys

<210> SEQ ID NO 37
<211> LENGTH: 21
<212> TYPE: PRT
<213> ORGANISM: Artificial Sequence
<220> FEATURE:
<223> OTHER INFORMATION: Synthetic Construct

<400> SEQUENCE: 37

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 38
<211> LENGTH: 18
<212> TYPE: PRT
<213> ORGANISM: Artificial Sequence
<220> FEATURE:
<223> OTHER INFORMATION: Synthetic Construct

<400> SEQUENCE: 38

Arg Gly Gly Arg Leu Ser Tyr Ser Arg Arg Arg Phe Ser Thr Ser Thr
1               5                   10                  15

Gly Arg

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Ser Asp Leu Trp Glu Met Met Met Val Ser Leu Ala Cys Gln Tyr
1               5                   10                  15

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Thr Ser Pro Leu Asn Ile His Asn Gly Gln Lys Leu
1               5                   10

<210> SEQ ID NO 41
<211> LENGTH: 8
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = Phe, Ile, Trp, or Leu

<400> SEQUENCE: 41

Leu Gly Leu Xaa Trp Xaa Xaa Xaa
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(7)
<223> OTHER INFORMATION: Xaa = any amino acid

<400> SEQUENCE: 42

Leu Gly Leu Xaa Trp Xaa Xaa Leu
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Arg Lys Lys Arg Arg Gln Arg Arg Arg Ala
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Ala Gly Ala Arg Ala Tyr Ala Ala
1               5
```